United States Patent
Yabuta et al.

(10) Patent No.: US 7,082,832 B2
(45) Date of Patent: Aug. 1, 2006

(54) SHEET MATERIAL IDENTIFYING DEVICE AND IMAGE FORMING APPARATUS HAVING SHEET MATERIAL IDENTIFYING DEVICE

(75) Inventors: Hisato Yabuta, Hiroshima (JP); Norio Kaneko, Kanagawa (JP); Takehiko Kawasaki, Kanagawa (JP); Ayanori Endo, Kanagawa (JP)

(73) Assignee: Canon Kabushiki Kaisha, Tokyo (JP)

(*) Notice: Subject to any disclaimer, the term of this patent is extended or adjusted under 35 U.S.C. 154(b) by 0 days.

(21) Appl. No.: 10/751,872

(22) Filed: Jan. 5, 2004

(65) Prior Publication Data

US 2004/0187579 A1    Sep. 30, 2004

(30) Foreign Application Priority Data

Jan. 6, 2003  (JP)  ............................. 2003-000709
Jan. 6, 2003  (JP)  ............................. 2003-000712

(51) Int. Cl.
*G01N 29/07*  (2006.01)
*G01N 29/12*  (2006.01)

(52) U.S. Cl. ..................... 73/597; 73/159; 347/19
(58) Field of Classification Search ................ 73/579, 73/597, 598, 602, 159; 347/19
See application file for complete search history.

(56) References Cited

U.S. PATENT DOCUMENTS

| | | | | |
|---|---|---|---|---|
| 4,080,836 A | * | 3/1978 | Thompson et al. | ............ 73/597 |
| 4,305,294 A | * | 12/1981 | Vasile et al. | ................... 73/579 |
| 4,372,163 A | * | 2/1983 | Tittmann et al. | .............. 73/597 |
| 4,976,150 A | * | 12/1990 | Deka | ........................... 73/644 |
| 5,934,140 A | | 8/1999 | Jackson et al. | |
| 6,561,509 B1 | | 5/2003 | Kettenmann et al. | |
| 6,866,263 B1 | | 3/2005 | Kawasaki | |
| 2003/0053089 A1 | | 3/2003 | Nojiri et al. | |
| 2003/0053090 A1 | | 3/2003 | Nojiri et al. | |

FOREIGN PATENT DOCUMENTS

| | | |
|---|---|---|
| JP | 55-022166 | 2/1980 |
| JP | 57-148231 | 9/1982 |
| JP | 08-050073 | 2/1996 |
| JP | 10-006607 | 1/1998 |
| JP | 10-027273 | 1/1998 |
| JP | 11-188898 | 7/1999 |
| JP | 2000-025261 | 1/2000 |
| JP | 2002-310866 | 10/2002 |

* cited by examiner

*Primary Examiner*—John E. Chapman
(74) *Attorney, Agent, or Firm*—Morgan & Finnegan, LLP

(57) ABSTRACT

A sheet material identifying device for identifying the kind of sheet material by applying vibration on the sheet material. The identifying device has a vibrator for applying vibration on the sheet material, a vibration sensor for detecting, via the sheet material, vibration applied by the vibrator, a device for changing a vibrating state between the vibrator and the vibration sensor, and an identifying section for identifying the kind of sheet material based on a detection result of the vibration sensor. Also, an image forming apparatus making use of the sheet material identifying device and a method of identifying the kind of sheet material are provided.

8 Claims, 16 Drawing Sheets

FREQUENCY f

DISTANCE x FROM REFERENCE POINT

DISTANCE b BETWEEN PICKUP AND VIBRATOR

SHEET MATERIAL IDENTIFYING DEVICE AND IMAGE FORMING APPARATUS HAVING SHEET MATERIAL IDENTIFYING DEVICE

BACKGROUND OF THE INVENTION

1. Field of the Invention

The present invention relates to a sheet material identifying device for identifying the kind of sheet material and an image forming apparatus having the sheet material identifying device.

2. Related Background Art

Conventionally sheet material identifying device for identifying sheet materials receive attention in various technical fields. For example, the number of kinds of paper used for printers has increased year by year and thus devices for identifying the kind of paper (overhead transparencies, photo glossy papers, coated papers or plain papers) have grown in demand. This point will be described below.

With the development of inkjet technology, ink-jet printers are capable of printing photos with high image quality. In this case, it is important to control an amount of ink discharged from an ink-jet printer to a sheet and control the penetration of ink, the control being made by treatment on a surface of a sheet. Hence, the ink discharge ports of ink-jet printers have been improved to be finer. Also regarding papers, ink penetration control has been improved by performing coating on a surface of a dedicated paper for high image quality. For this reason, a dedicated paper for high image quality is used for printing a high-quality image and a plain paper is used for ordinary printing. The dedicated paper for high image quality is inevitably expensive due to surface treatment. Depending upon desired image quality, several grades of papers are available. Prices correspond to the grades of papers. Further, overhead transparencies, though not being papers, are still used as a kind of printer paper. In this way, the variety of printer papers has become wider.

With such a variety of papers, it is necessary to change the setting of a printer for each kind of paper. When a setting is manually changed by the user, in the case where the user mistakenly selects a kind of paper or mistakenly makes a setting for paper, characters may be simply printed on an expensive dedicated paper for high picture quality.

Hence, the necessity for means and a device for identifying the kind of paper has become a focus of attention in recent years and the development of the means and device has been advanced.

In ink-jet printers currently on the market, devices for identifying the kind of paper emit light on a surface of a sheet by using a light-emitting element and detects reflected light and scattered light by using a light-receiving element. When a specific light beam is emitted to the surface of the sheet, reflected light and scattered light are varied due to gloss and roughness on the surface. The above-described device identifies the kind of paper in compliance with this principle. This technique is disclosed in U.S. Pat. No. 6,291,829.

However, such an optically detecting method requires a light-emitting source and detecting means including a lens for detecting reflected light, scattered light and transmitted light, resulting in a large number of components constituting the sheet detecting device.

SUMMARY OF THE INVENTION

An object of the present invention is to provide a sheet material identifying device capable of identification without using an optical component such as a lens, and an image forming apparatus having the sheet material identifying device.

A first invention of the present application is devised in view of the above-described circumstances and provides a sheet material identifying device for identifying the kind of sheet material by applying vibration on the sheet material comprising a vibrator for applying vibration on the sheet material, a vibration sensor for detecting, via the sheet material, vibration applied by the vibrator, means for changing a vibrating state between the vibrator and the vibration sensor, and an identifying section for identifying the kind of sheet material based on a detection result of the vibration sensor.

Further, a second invention provides an image forming apparatus comprising the above described sheet material identifying device, and an image forming section for forming an image on a sheet material based on information corresponding to the kind of sheet material identified by the sheet material identifying device.

Moreover, a third invention provides a method of identifying the kind of sheet material by applying vibration on the sheet material comprising the steps of applying vibration to the sheet material by using a vibrator, detecting the vibration applied to the sheet material, via the sheet material by using the vibration sensor, changing a vibrating state between the vibrator and the vibration sensor, and identifying the kind of sheet material based on a detection result which is changed according to the changed vibration state from the vibration sensor.

BRIEF DESCRIPTION OF THE DRAWINGS

FIG. 10 is a diagram showing the relationship between an amplitude of a signal detected by the vibration sensor and a moving distance of the vibrator and so on;

FIG. 11 is a diagram showing the relationship between an amplitude of a signal detected by the vibration sensor and a moving distance of the vibrator and so on;

DESCRIPTION OF THE PREFERRED EMBODIMENTS

Referring to FIGS. 1 to 17, the embodiment of the present invention will be described below.

Figure 1:
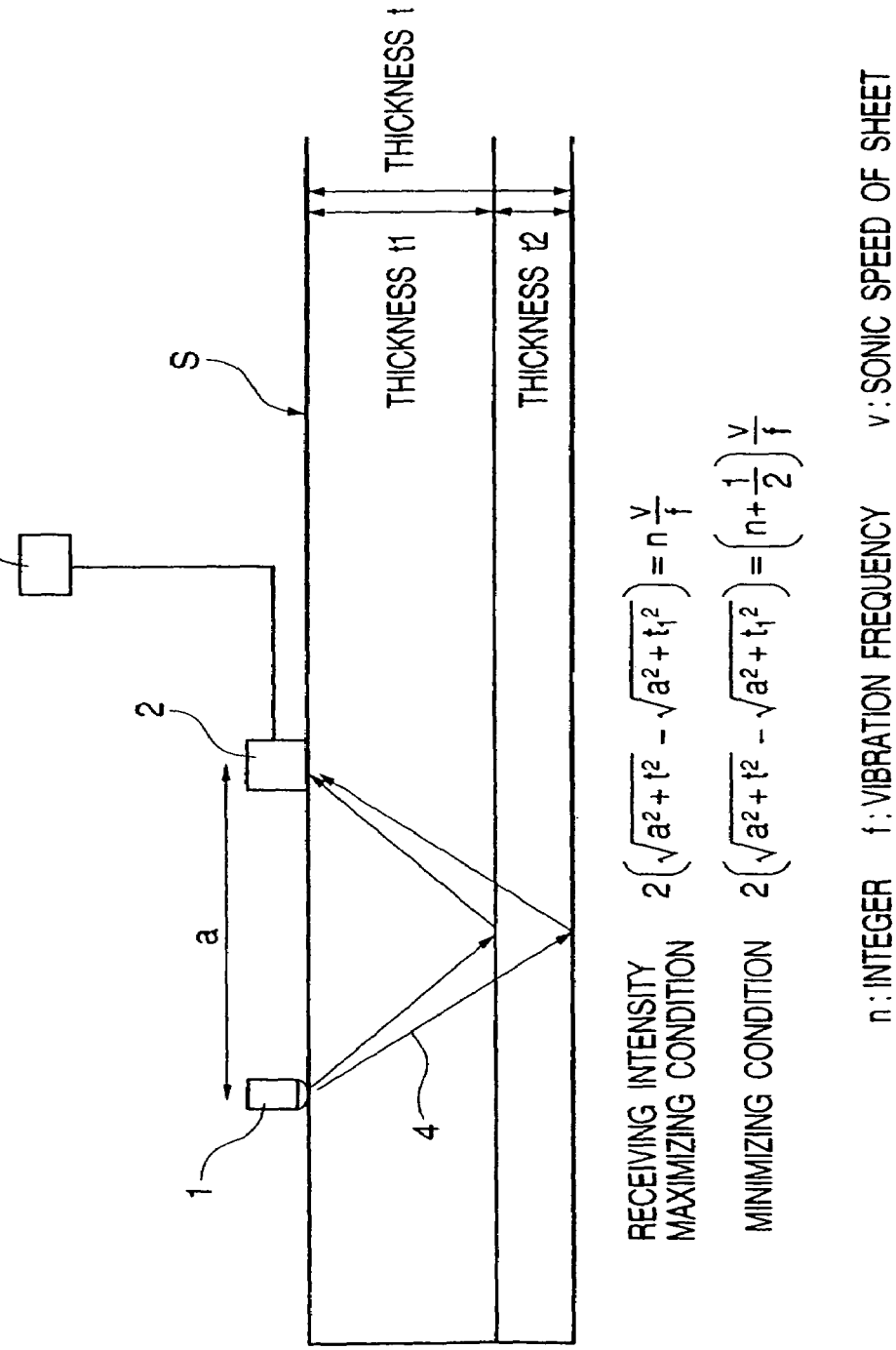
FIG. 1 is a schematic diagram showing an example of the configuration of a sheet material identifying device according to the present invention.

As shown in FIG. 1, a sheet material identifying device of the present embodiment comprises:

a vibrator 1 making contact with a sheet material S to propagate an acoustic wave through the sheet material S, a vibration sensor 2 making contact with the sheet material S to detect an acoustic wave having propagated through the sheet material S, and an identifying section 3 for identifying the kind of the sheet material S based on the detection result of the vibration sensor 2.

Figure 2:
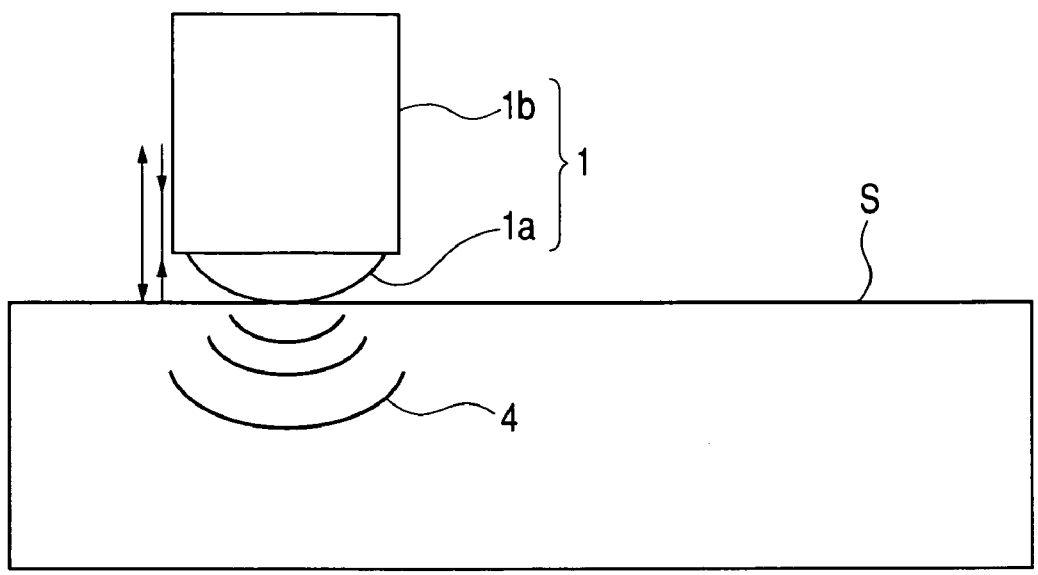
FIG. 2 is a schematic diagram showing an example of the configuration of a vibrator.

When the kind of sheet material is identified,
the vibration frequency of the vibrator 1 is changed, or the position of the vibrator 1 or the vibration sensor 2 is changed so that a distance a between the vibrator 1 and the vibration sensor 2 is changed. Further, as shown in FIG. 2, the vibrator 1 has a convex portion 1a which is brought into contact with the sheet material S.

Then, the convex portion 1a is brought into contact with the sheet material S, so that a semispherical wave (reference numeral 4 in FIG. 2) is emitted from the vibrator 1 to the sheet material S. The acoustic wave is reflected on the undersurface or the layer interface of the sheet material S and is detected by the vibration sensor 2. As described above, when the position of the vibrator 1 or the vibration sensor 2 is changed or when the sheet material is varied in thickness and thus the position of reflecting an acoustic wave is varied, the acoustic wave propagating into the vibration sensor 2 is varied in incident angle. However, since the semispherical wave has little directivity (anisotropy), it is possible to minimize the influence (change in receiving conditions) of the incident angle of the acoustic wave propagating into the vibration sensor.

It is preferable that the above-described vibrator 1 is constituted of the convex portion 1a and a portion 1b (hereinafter, referred to as a "vibration generating element") for generating vibration. In this case, the vibration generating element 1b includes a piezoelectric body illustrated in FIG. 3. Further, it is preferable to join the convex portion 1a and the vibration generating element 1b. The convex portion 1a is made of a material selected from the group consisting of a ceramic material including alumina and silica and a metallic material including tantalum and molybdenum that have excellent resistance to abrasion.

When a surface acoustic wave is used, the vibrator may have a vibration generating element directly making contact with a surface of the sheet material.

In this case, it is preferable that a power supply for generating alternating voltage is connected to the vibration generating element 1 and the frequency can be arbitrarily changed (will be described in detail later). Moreover, it is preferable that an amplifier (not shown) for amplifying a detection signal and a signal processor are connected to the vibration sensor 2 and the identifying section 3 is further connected to the vibration sensor 2.

Further, it is preferable to apply a given load (load for bringing the element into close contact with the sheet material) to the vibration generating element 1 and the vibration sensor 2.

In the example of FIG. 1, the vibrator 1 and the vibration sensor 2 are a predetermined distance a away from each other on one side of the sheet material S and the identifying section 3 identifies the kind of sheet material from the detection result of the vibration sensor 2 based on a change in the vibration frequency of the vibrator 1. The configuration is not particularly limited.

For example, the following configuration is also applicable: the vibrator 1 and the vibration sensor 2 are the predetermined distance a away from each other on one side of the sheet material S in the above-described manner, the identifying section 3 identifies the kind of sheet material from the detection result of the vibration sensor 2 by changing the position of at least one of the vibrator 1 and the vibration sensor 2 (that is, the distance a between the vibrator 1 and the vibration sensor 2 is changed) instead of changing the vibration frequency of the vibrator 1. The sheet material identifying device is premised on a configuration where the vibrator 1 and the vibration sensor 2 are in contact with the sheet material S. Thus, "the positions of the vibrator 1 and the vibration sensor 2 are changed" means movement along the sheet material S (this applies also in the following description).

Figure 4:
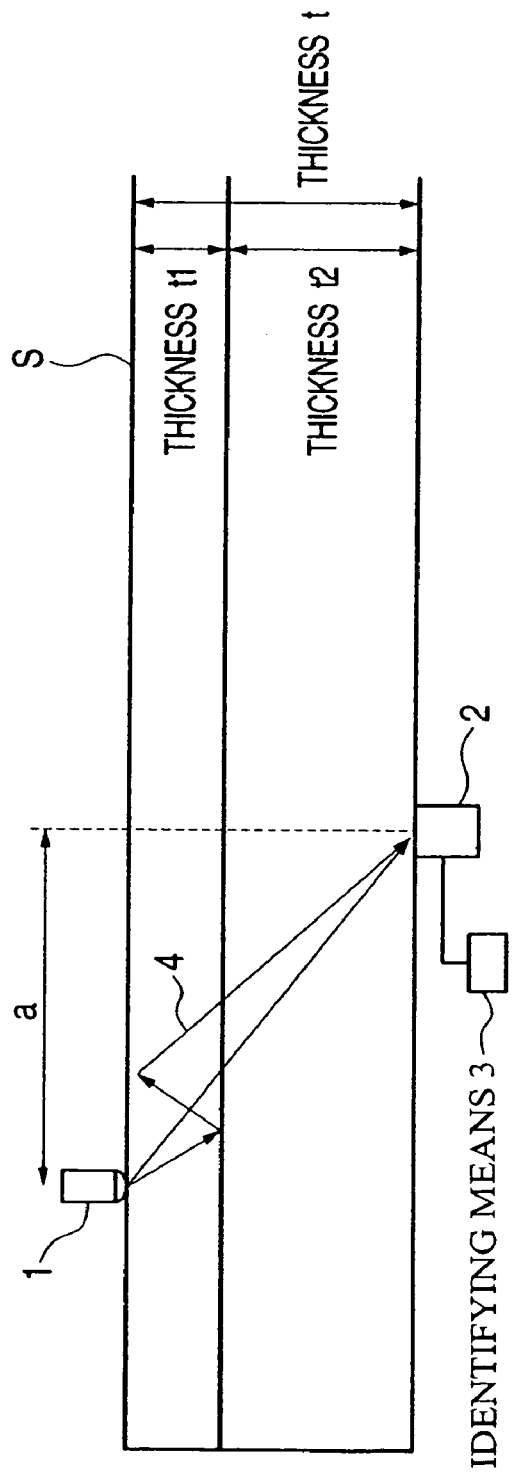
FIG. 4 is a schematic diagram showing an example of the configuration of the sheet material identifying device according to the present invention.

Further, as shown in FIG. 4, the identifying section 3 may identify the kind of sheet material from the detection result of the vibration sensor 2 based on the configuration where the vibrator 1 and the vibration sensor 2 are disposed respectively on the sides of the sheet material S and the vibration frequency of the vibrator 1 is changed.

Moreover, the following configuration is also applicable: the vibrator 1 and the vibration sensor 2 are disposed respectively on the sides of the sheet material S in the above-described manner, the identifying section 3 identifies the kind of sheet material from the detection result of the vibration sensor 2 by changing the position of at least one of the vibrator 1 and the vibration sensor 2 (that is, the distance a between the vibrator 1 and the vibration sensor 2 is changed) instead of changing the vibration frequency of the vibrator 1.

Figure 5:
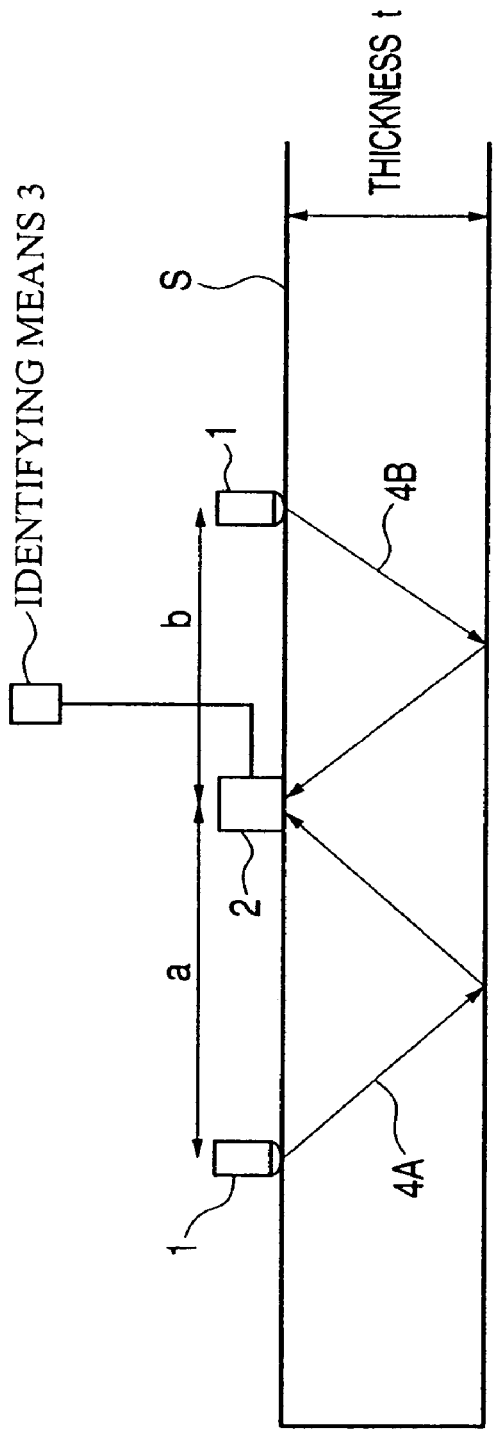
FIG. 5 is a schematic diagram showing an example of the configuration of the sheet material identifying device according to the present invention.

Furthermore, as shown in FIG. 5, the following configuration is also applicable: two or more vibrators 1 are disposed on one side of the sheet material S, one vibration sensor 2 is disposed on the same side as the vibrators 1, and different distances a and b are set between the vibrators 1 and the vibration sensor 2. In such a configuration, an acoustic wave 4A reaching the vibration sensor 2 from one of the vibrators 1 and an acoustic wave 4B reaching the vibration sensor 2 from the other vibrator 1 interfere with each other. When all the vibrators 1 are similarly changed in vibration frequency at the same time, the identifying section 3 can identify the kind of sheet material from the detection result of the vibration sensor 2. FIG. 5 shows the two vibrators 1 and one vibration sensor 2. Needless to say, the configuration is not particularly limited. Three or more vibrators 1 and two or more vibration sensors 2 may be provided (this applies to FIGS. 6 to 8 as well).

Moreover, the following configuration is also applicable: two or more vibrators 1 and one vibration sensor 2 are disposed on one side of the sheet material S in the above-described manner, the identifying section 3 identifies the kind of sheet material from the detection result of the vibration sensor 2 by changing the position of at least one of the vibrators 1 and the vibration sensor 2 (that is, the distance a or b between the vibrators 1 and the vibration sensor 2 is changed) instead of changing the vibration frequency of the vibrator 1.

Figure 6:
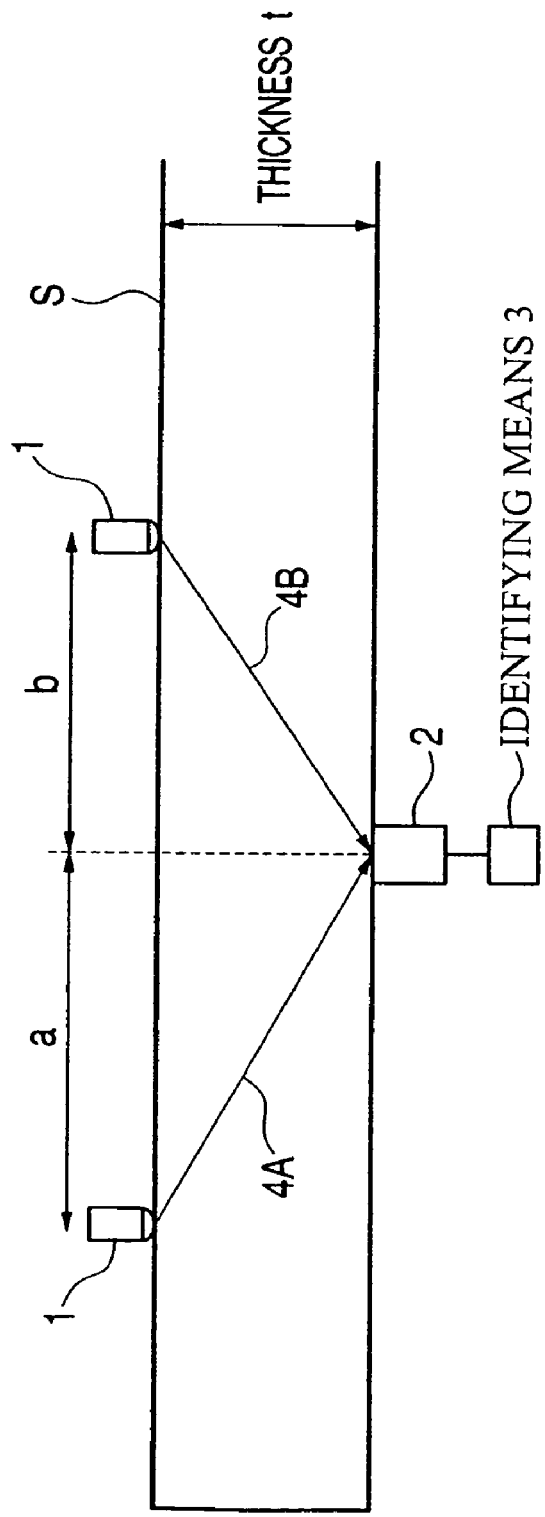
FIG. 6 is a schematic diagram showing an example of the configuration of the sheet material identifying device according to the present invention.

Further, as shown in FIG. 6, the following configuration is also applicable: two or more vibrators 1 are disposed on one side of the sheet material S, the vibration sensor 2 is disposed on the other side of the sheet material S, and different distances a and b are set between the vibrators 1 and the vibration sensor 2. In this configuration, the acoustic wave 4A reaching the vibration sensor 2 from one of the vibrators 1 and the acoustic wave 4B reaching the vibration sensor 2 from the other vibrator 1 interfere with each other. When all the vibrators 1 are similarly changed in vibration frequency at the same time, the identifying section 3 identifies the kind of sheet material from the detection result of the vibration sensor 2.

Besides, the following configuration is also applicable: two or more vibrators 1 are disposed on one side of the sheet material S, one vibration sensor 2 is disposed on the other side of the sheet material S, and different distances a and b are set between the vibrators 1 and the vibration sensor 2, the identifying section 3 identifies the kind of sheet material from the detection result of the vibration sensor 2 by changing the position of at least one of the vibrators 1 and the vibration sensor 2 (that is, the distance a or b between the vibrators 1 and the vibration sensor 2 is changed) instead of simultaneously changing the vibration frequencies of all the vibrators 1 in a similar manner.

Figure 7:
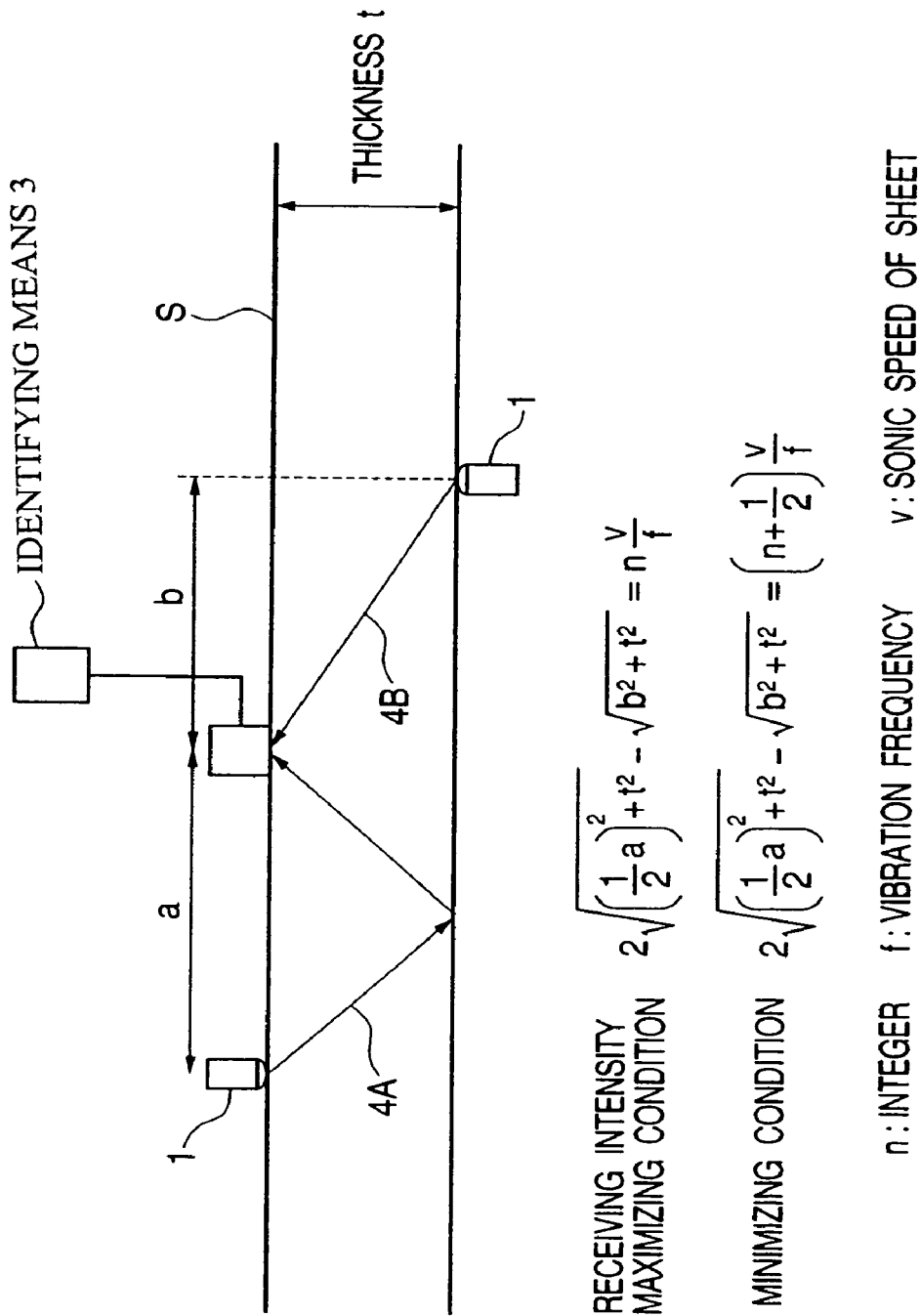
FIG. 7 is a schematic diagram showing an example of the configuration of the sheet material identifying device according to the present invention.
Figure 8:
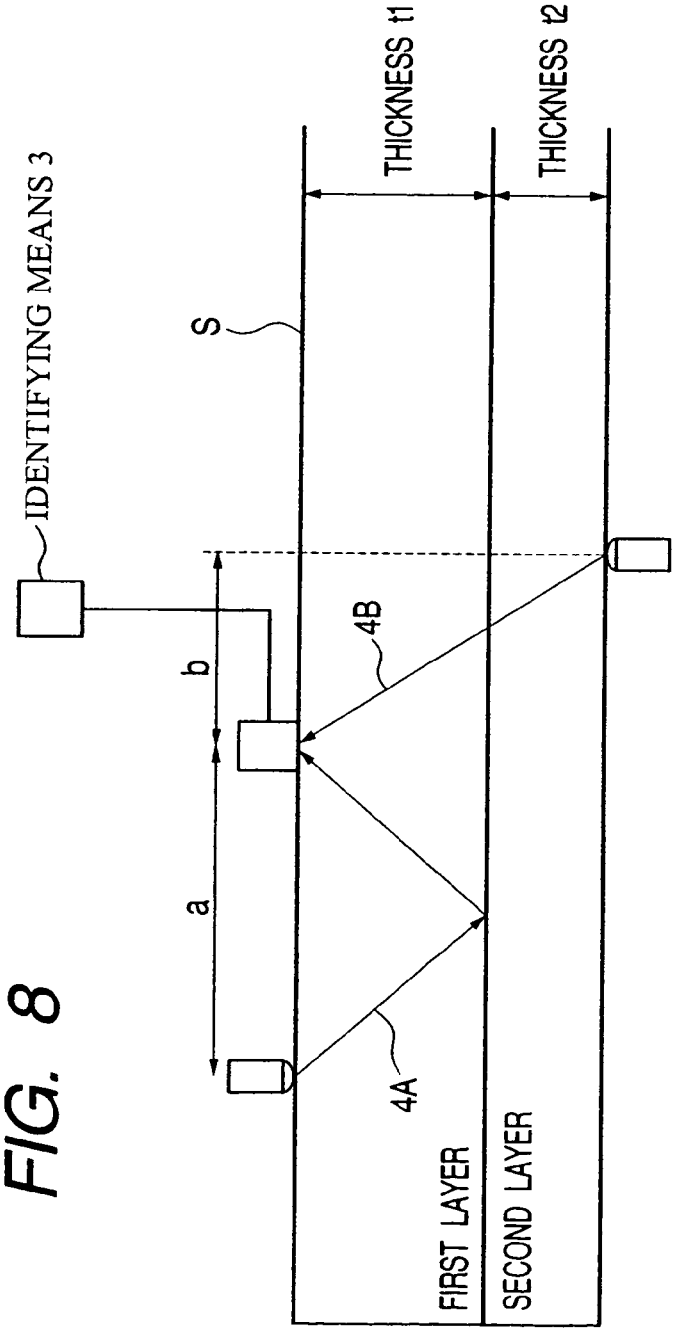
FIG. 8 is a schematic diagram showing an example of the configuration of the sheet material identifying device according to the present invention.

As shown in FIGS. 7 and 8, the following configuration is also applicable: one or more vibrators 1 are disposed respectively on the sides of the sheet material S, one vibration sensor 2 is disposed on one side of the sheet material S, and different distances a and b are set between the vibrators 1 and the vibration sensor 2. In this configuration, the acoustic wave 4A reaching the vibration sensor 2 from one of the vibrators 1 and the acoustic wave 4B reaching the vibration sensor 2 from the other vibrator 1 interfere with each other. When the vibration frequencies of all the vibrators 1 are similarly changed at the same time, the identifying section 3 identifies the kind of sheet material from the detection result of the vibration sensor 2.

The following configuration is also applicable: in a similar manner, one or more vibrators 1 are disposed respectively on the sides of the sheet material S, one vibration sensor 2 is disposed on one side of the sheet material, different distances a and b are set between the vibrators 1 and the vibration sensor 2, and the identifying section 3 identifies the kind of sheet material from the detection result of the vibration sensor 2 by changing the position of at least one of the vibrators 1 and the vibration sensor 2 (that is, the distance a or b between the vibrators 1 and the vibration sensor 2 is changed) instead of simultaneously changing the vibration frequencies of all the vibrators 1 in a similar manner.

For identification of a sheet material, the following methods are available:

a method of changing a frequency of vibration (hereinafter, referred to as a "vibration frequency") generated on the vibration generating element 1, and a method of changing a positional relationship between the vibration generating element 1 and the vibration sensor 2. The following will describe these methods in detail.

Figure 9:
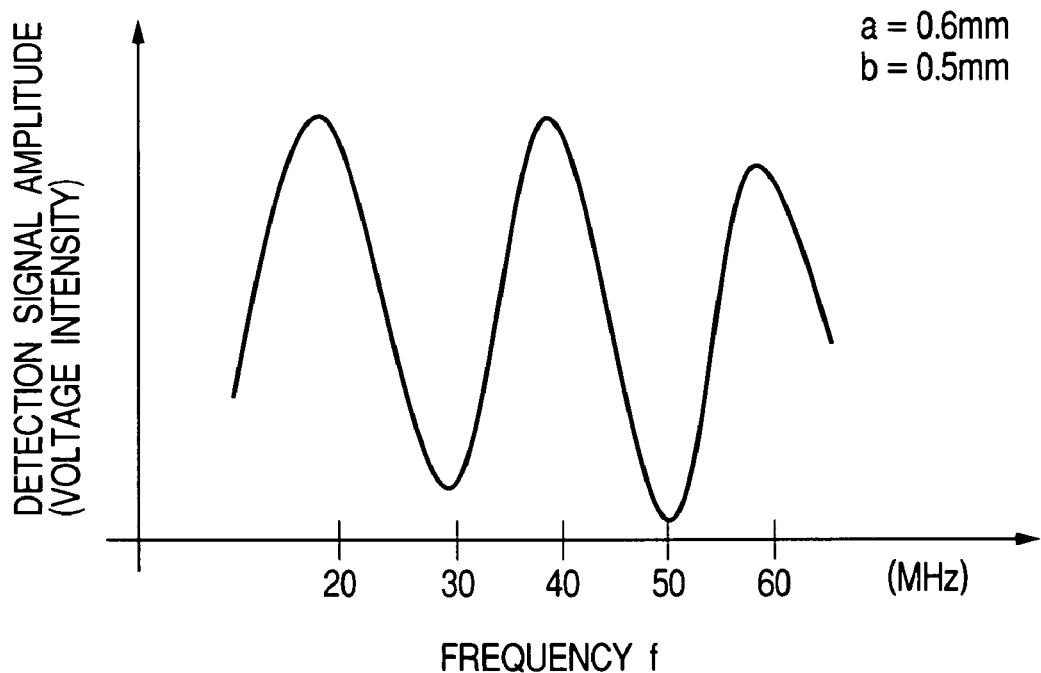
FIG. 9 is a diagram showing the relationship between a vibration frequency and an amplitude of a signal detected by a vibration sensor.
Figure 10:
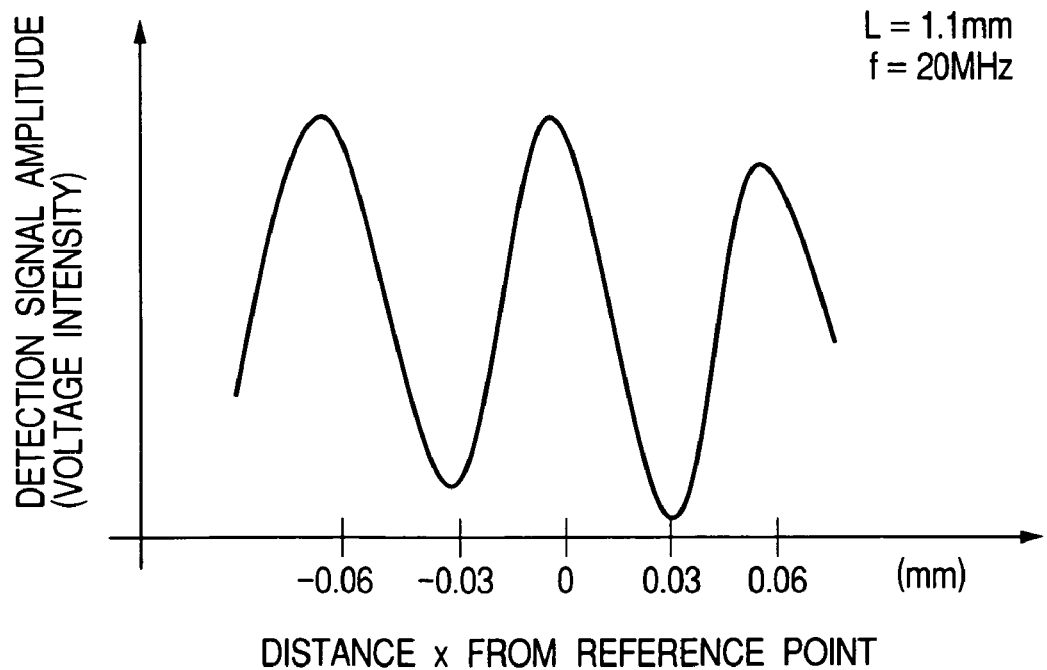
Figure 11:
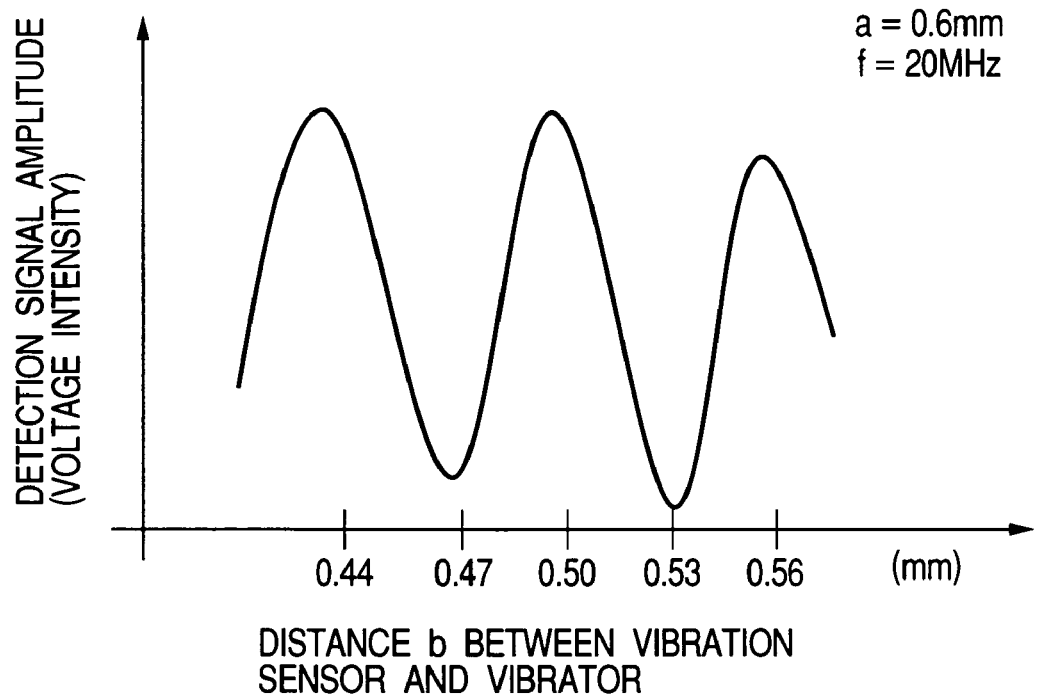
Figure 13:
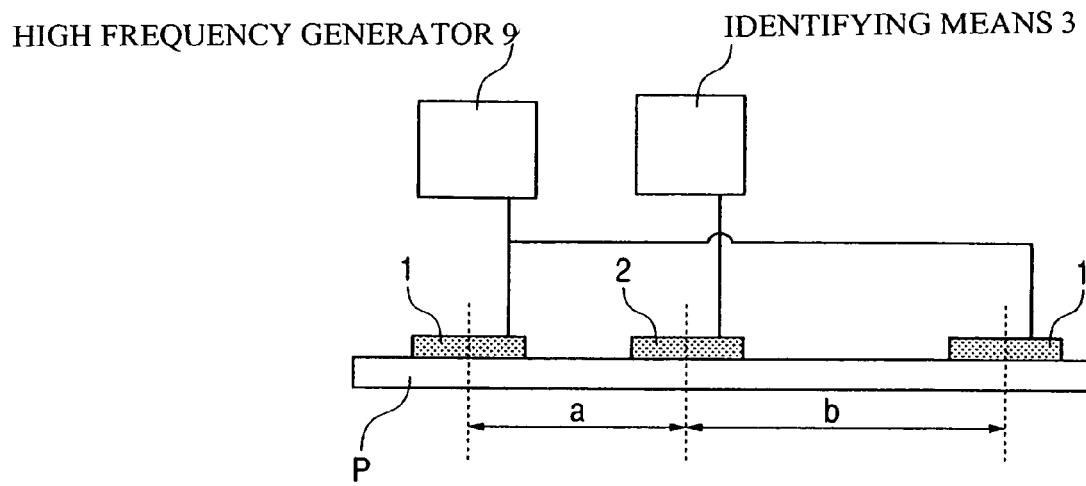
FIG. 13 is a sectional view showing an example of the configuration of the sheet material identifying device according to the present invention.

When the vibration frequency of the vibration generating element 1 is changed, the following setting is preferable:

the distance a between one of the vibration generating element 1 and the vibration sensor 2 is set so as to be different from the distance b between the other vibration generating element 1 and the vibration sensor 2 (a distance between the vibration generating element 1 and the vibration sensor 2 along a sheet material P, and the distance is equivalent to a distance of projection performed on the sheet material P when the vibration generating element 1 and the vibration sensor 2 are disposed on the different sides of the sheet material P as shown in FIG. 6 and so on), and the sheet material is identified based on a detection signal of the vibration sensor 2 when the vibration generating element 1 is changed in vibration frequency. In a process of changing a vibration frequency, it is preferable to make equal the vibration frequencies of the vibration generating elements 1. When the vibration generating elements 1 generate vibration, the vibrations interfere with each other during propagation through the sheet material. The interference is detected by the vibration sensor 2 and the amplitude of the detection signal is changed according to a vibration frequency. For example, when the vibration generating elements 1 and the vibration sensor 2 are arranged as shown in FIG. 13, vibration generated by the vibration generating element 1 propagates through the sheet material, is reflected on the opposed surfaces of the sheet material, and reaches the vibration sensor 2. The detection signal of the vibration sensor 2 is changed in amplitude as shown in FIG. 9:

at a frequency satisfying a receiving intensity maximizing condition (Formula 1), vibrations generated on the two vibration generating elements 1 increase each other and the amplitude of the detection signal has a maximum value (Formula 2), and conversely, at a frequency satisfying a receiving intensity minimizing condition, vibrations generated on the two vibration generating elements 1 reduce each other and the amplitude of the detection signal has a minimum value $$a - b = n\frac{v}{f} \quad \text{[Formula 1]}$$

$$a - b = \left(n + \frac{1}{2}\right)\frac{v}{f} \quad \text{[Formula 2]}$$

wherein n: integer
    f: vibration frequency
    v: sonic speed

In the characteristic curve of FIG. 9, the differences listed below are varied according to a propagating speed (i.e., sonic speed) of vibration in the sheet material and a thickness of the sheet material:

a difference (frequency difference) between a frequency where the detection signal has a maximum value and a frequency where the detection signal has another maximum value, a difference (frequency difference) between a frequency where the detection signal has a minimum value and a frequency where the detection signal has another minimum value, and a difference (frequency difference) between a frequency where the detection signal has a maximum value and a frequency where the detection signal has a minimum value.

Thus, the identifying means 3 determines the frequency difference in consideration of the thickness of the sheet material, so that the sheet material is determined. When the sheet material has a multilayer structure composed of a plurality of layers, vibration is reflected on each layer interface. Thus, the dependence of the receiving intensity on a frequency is changed according to a sonic speed (v) of each layer and a thickness (t1, t2, . . . ) of each layer in the sheet material. A frequency difference of an interference peak of vibration has a value specific to the kind of sheet material, so that the kind of sheet material can be identified.

Further, when the positional relationship between the vibration generation elements 1 and the vibration sensor 2 is changed, it is preferable that:

all the vibration generating elements 1 have equal and constant vibration frequencies, and the sheet material is identified based on the detection signal of the vibration sensor 2 when the vibration generating element 1 or the vibration sensor 2 is moved.

Figure 14:
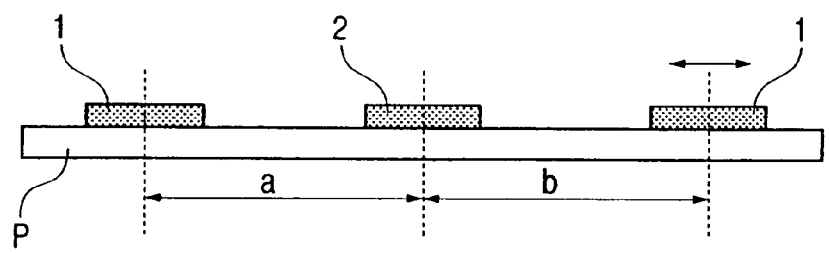
FIG. 14 is a sectional view showing an example of the configuration of the sheet material identifying device according to the present invention.
Figure 15:
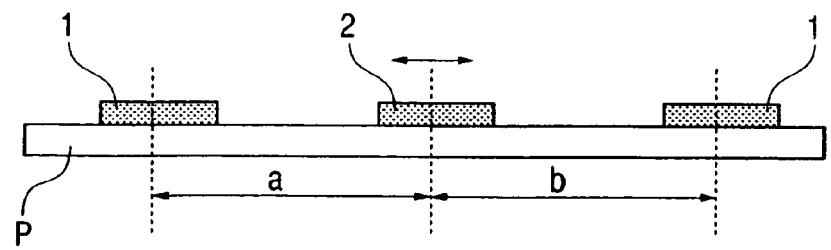
FIG. 15 is a sectional view showing an example of the configuration of the sheet material identifying device according to the present invention.

FIG. 14 is a schematic diagram showing that the vibration generating elements 1 are moved. FIG. 15 is a schematic diagram showing that the vibration sensor 2 is moved. Before the elements 1 and 2 start moving, the distances (i.e., the distance a between one of the vibration generating element 1 and the vibration sensor 2 and the distance b between the other vibration generating element 1 and the vibration detecting element 2) may be equal to each other or different from each other. When the vibration generating elements 1 generate vibration, the vibrations interfere with each other during propagation through the sheet material. The interference is detected by the vibration sensor 2 and the amplitude of the detection signal is changed according to a difference "a–b" of the distances:

at "a–b" satisfying the receiving intensity maximizing condition, vibrations generated by the two vibration generating elements 1 increase each other and the amplitude of the detection signal has a maximum value, and conversely, at "a–b" satisfying the receiving intensity minimizing condition, vibrations generated by the two vibration generating elements 1 reduce each other and the amplitude of the detection signal has a minimum value.

In the characteristic curve, the differences listed below are varied according to a propagating speed (i.e., sonic speed) of vibration in the sheet material and a thickness of the sheet material:

a difference between a value where the detection signal has a maximum value and a value where the detection signal has another maximum value, a difference between a value where the detection signal has a minimum value and a value where the detection signal has another minimum value, and a difference between a value where the detection signal has a maximum value and a value where the detection signal has a minimum value.

Thus, the identifying means 3 determines the difference in consideration of the thickness of the sheet material, so that the sheet material is determined.

The vibration generating element 1 may be:

a vibration element for inducing a surface acoustic wave traveling only in a specific direction, and a vibration element for inducing vibration traveling in a wide-range direction.

The vibration'sensor 2 may be:

a vibration sensor for detecting a surface acoustic wave in a specific direction, and a vibration sensor for detecting vibration from a wide-range direction.

Figure 16:
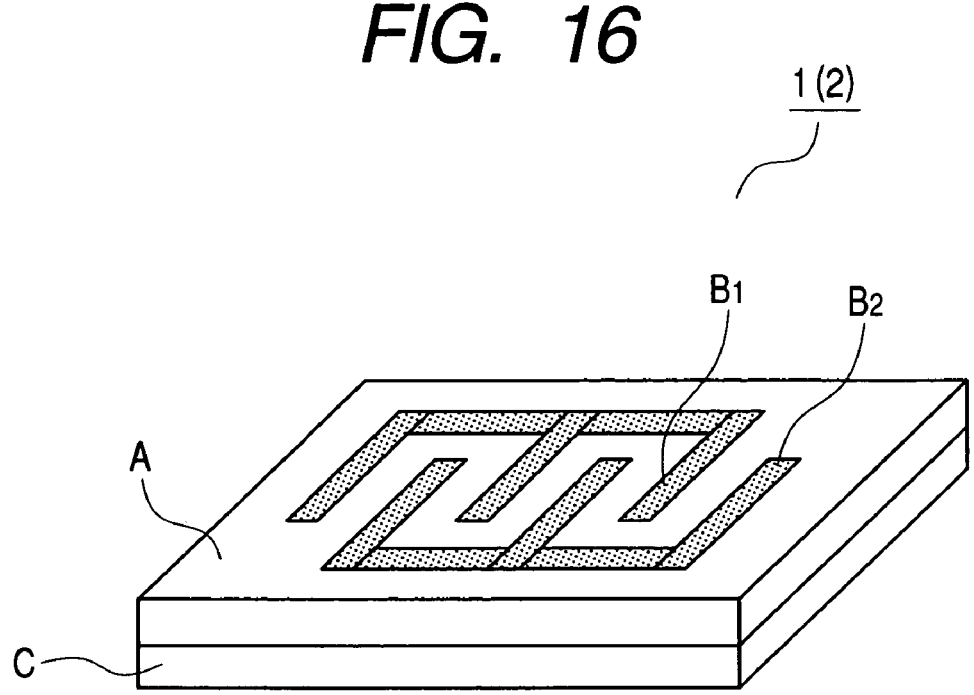
FIG. 16 is an outside perspective view showing the configuration of a vibration generating element and a vibration sensor.

As shown in FIG. 16, it is preferable that the vibration generating element 1 and the vibration sensor 2, which induce or detect an elastic wave traveling in a specific direction, are constituted of a piezoelectric body A and electrodes B1 and B2. It is preferable that the piezoelectric body A is supported by a silicon substrate C and so on and is formed by the sputtering method, CVD, laser abrasion, and so on. Moreover, the piezoelectric body A is preferably made of a material selected from the group consisting of zinc oxide and PZT. Further, it is preferable to use, as the electrodes B1 and B2, comb-shaped electrodes opposed to each other. The electrodes B1 and B2 are preferably formed on a surface of the piezoelectric body A. It is preferable that the electrodes B1 and B2 and the piezoelectric body A are caused to be flush with one another by using photolithography, etching, and so on. The electrodes B1 and B2 are preferably made of a material selected from the group consisting of gold and platinum.

Figure 17:
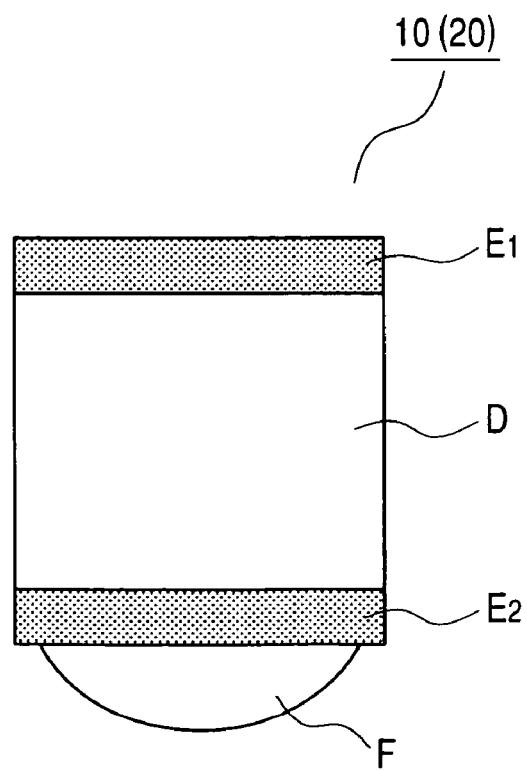
FIG. 17 is a side view showing the configuration of the vibration generating element and the vibration sensor.

In contrast, as shown in FIG. 17, the vibration generating element 10 and the vibration sensor 20, which induce or detect an elastic wave from a wide-range direction, are preferably constituted of a piezoelectric body D and electrodes E1 and E2 formed on both surfaces (opposing surfaces) of the piezoelectric body D. The piezoelectric body D is preferably made of a material selected from the group consisting of oxide ceramics including zinc titanate zirconate, barium titanate, and zinc oxide. The electrodes E1 and E2 may be made of a material selected from the group consisting of metals including gold, platinum, silver (or an alloy composed of the metals) or may be composed of oxide electrodes made of a material selected from the group consisting of ITO (indium tin oxide) and zinc oxide. Then a portion F making contact with the sheet material is preferably attached to the electrode E2. The portion F is preferably made of a material having high resistance to abrasion. Further, the portion F is preferably formed into a sphere to obtain a wide-range propagating direction of an elastic wave. Instead of the piezoelectric body D and the electrodes E1 and E2, it is possible to adopt a magnetostrictor and a coil, a permanent magnet and a coil, or a motor and a clamp.

Incidentally, the following configuration is also applicable: at least one vibration generating element is disposed, a plurality of vibration sensors are disposed, and the identifying means identifies the kind of sheet material based on the detection signal of the vibration sensors.

In this case, the vibration generating element and the plurality of vibration sensors may be in contact with a surface of the sheet material, and the plurality of vibration sensors may be in contact with a surface of the sheet material and the vibration generating element may be in contact with the other surface of the sheet material, and further at least one vibration generating element and at least one vibration sensor may be in contact with a surface of the sheet material and at least one vibration sensor may be in contact with the other surface of the sheet material.

Besides, the vibration generating element and the plurality of vibration sensors may be disposed respectively on the sides of the sheet material to perform detection on both sides of the sheet material.

As a method for identifying a sheet material, the following method is available: a distance between one vibration sensor and the vibration generating element and a distance between the other vibration sensor and the vibration generating element are set so as to be different from each other, and the sheet material is identified based on the detection signal of the plurality of vibration sensors when vibration generated by the vibration generating element is changed in frequency. In this case, the identifying means preferably identifies the sheet material based on a difference between a frequency where the detection signal has a maximum value and a frequency where the detection signal has another maximum value, a difference between a frequency where the detection signal has a minimum value and a frequency where the detection signal has another minimum value, and a difference between a frequency where the detection signal has a maximum value and a frequency where the detection signal has a minimum value.

Another method for identifying a sheet material may be adopted as follows: vibration of a given frequency is generated from the vibration generating element, and a sheet material is identified based on the detection signal of the plurality of vibration sensors when the vibration generating element or the vibration sensors are moved. In this case, the identifying means preferably identifies the sheet material based on a difference between a value where the detection signal has a maximum value and a value where the detection signal has another maximum value, a difference between a value where the detection signal has a minimum value and a value where the detection signal has another minimum value, and a difference between a value where the detection signal has a maximum value and a value where the detection signal has a minimum value. An element generating a surface acoustic wave is applicable as the vibration generating element, and an element detecting a surface acoustic wave is applicable as the vibration sensor.

Besides, it is preferable to distinguish among kinds of paper, that is, plain papers, overhead transparencies, coated papers (paper coated with alumina and so on), and glossy papers by using the sheet material identifying device configured thus. Further, the sheet material identifying device is mounted in an image forming apparatus to identify the kind of print paper which serves as a recording medium.

EXAMPLES

The present invention will be described in detail with reference to the following examples.

Example 1

Figure 3:
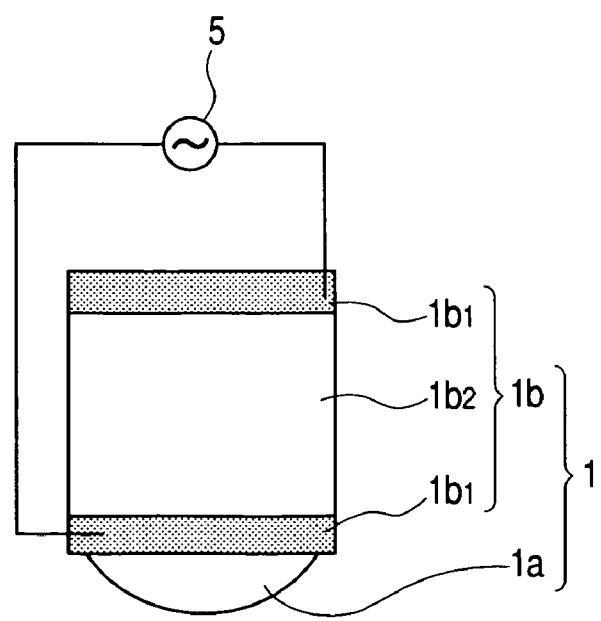
FIG. 3 is a schematic diagram showing an example of the configuration of a vibrator.
Figure 12:
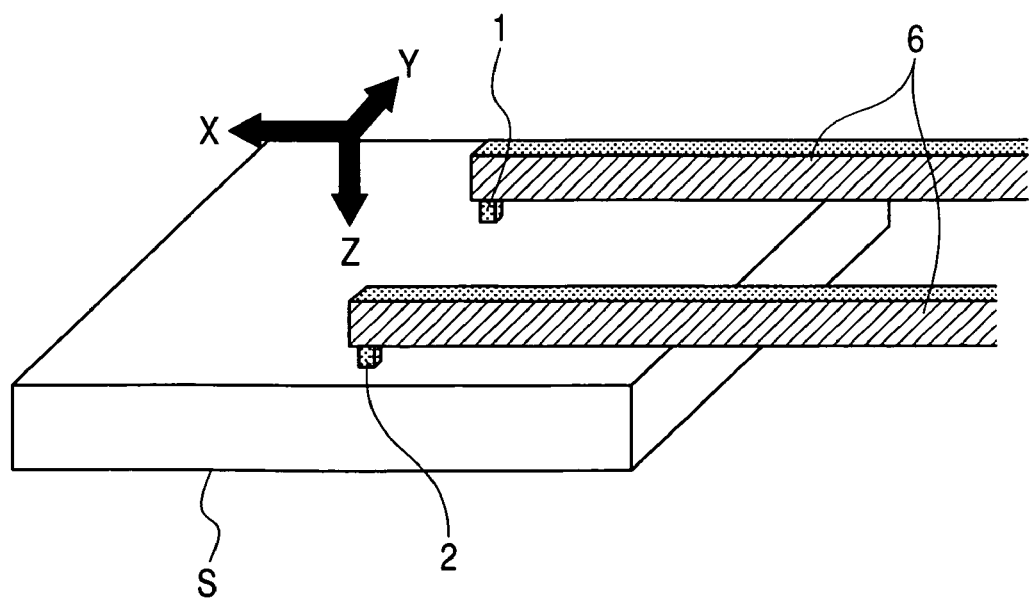
FIG. 12 is a perspective view showing an example of the structure of the sheet material identifying device according to the present invention.

In the present example, a sheet material identifying device shown in FIGS. 1, 3, and 12 was fabricated.

As shown in FIG. 3, a vibrator 1 was constituted of a convex portion 1*a* and a vibration generating element 1*b*. A piezoelectric body 1*b*2 having electrodes 1*b*1 bonded to both sides was used as the vibration generating element 1*b*. The piezoelectric body 1*b*2 was 0.2 mm in thickness along a voltage applying direction and had a surface size of 0.1 mm×0.1 mm. Further, a sphere made of alumina with a radius of 0.1 mm was used as the convex portion 1*a*, and the convex portion 1*a* and the vibration generating element 1*b* were brought into contact with each other. Moreover, the electrode 1*b*1 was connected to an alternating-current power supply 5 to enable alternating voltage at a given frequency to be applied to the piezoelectric body 1*b*2.

On the other hand, a vibration sensor 2 was composed of a piezoelectric body of 0.1 mm×0.1 mm×0.1 mm, and an alternating current voltmeter was used as an identifying section 3.

As shown in FIG. 12, the vibrator 1 and the vibration sensor 2 were attached to manipulators 6, respectively. As shown in FIG. 1, the vibrator 1 and the vibration sensor 2 were brought into contact with one side of a glossy paper S for an ink jet printer. A distance a between the vibrator 1 and the vibration sensor 2 was set at 1 mm. In this state, an alternating voltage with an amplitude of 20 V was applied from the alternating-current power supply 5 to the vibrator 1 and the frequency was changed from 0 to 70 MHz. The relationship between a frequency and an amplitude of a signal detected by the vibration sensor 2 is plotted in FIG. 9. Since a difference between adjacent maximum frequencies is different for each kind of paper, the kind of paper can be identified based on a frequency difference.

Example 2

In the present example, a vibrator 1 and a vibration sensor 2 are arranged as Example 1 (FIG. 1), a vibration frequency was not changed and was kept at a constant vibration frequency (20 MHz), and manipulators 6 were operated to move the vibration sensor 2. To be specific, the vibration sensor 2 is moved by 0.1 mm in a direction of approaching the vibrator 1, was returned to the original position, and was moved by 0.1 mm in a direction of moving away from the vibrator 1. The relationship between an amplitude of a signal detected by the vibration sensor 2 and a distance x from the reference point is plotted in FIG. 10. Since a difference between adjacent maximum distances is different for each kind of paper, the kind of paper can be identified based on a distance difference.

Example 3

In the present example, a sheet material identifying device shown in FIG. 5 was manufactured. Vibrators 1 and a vibration sensor 2 were configured as Example 1. Further, a distance a+b between one vibrator 1 and the other was set at 1.1 mm, and a distance a between one of the vibrators 1 and the vibration sensor 2 was set at 0.6 mm. A glossy paper for an ink jet printer was used as a sheet material S. An alternating-current power supply 5 applied a voltage of 20 V to each of the vibrators 1, 1, and the frequency was similarly changed from 0 to 70 MHz. The relationship between a frequency and an amplitude of a signal detected by the vibration sensor 2 is plotted in FIG. 9. Since a difference between adjacent maximum frequencies is different for each kind of paper, the kind of paper can be identified based on a frequency difference.

Example 4

In the present example, vibrators 1, 1 and a vibration sensor 2 were arranged as Example 3, a vibration frequency was not changed and was kept at a constant vibration frequency (20 MHz), and manipulators were operated to move the vibration sensor 2. To be specific, the vibration sensor 2 was moved so as to approach one of the vibrators 1 from the midpoint position between the vibrators 1, 1, was returned to the original position, and was moved so as to approach the other vibrator 1. The relationship between an amplitude of a signal detected by the vibration sensor 2 and a distance from the reference position is plotted in FIG. 10. Since a difference between adjacent maximum distances is different for each kind of paper, the kind of paper can be identified based on a distance difference.

The vibrator 1 may be moved instead of the vibration sensor 2. For example, a distance a between one of the vibrators 1 and the vibration sensor 2 may be fixed at 0.6 mm and the other vibrator 1 may be moved. In this case, the relationship between an amplitude of a signal detected by the vibration sensor 2 and a distance b is plotted in FIG. 11. Since a difference between adjacent maximum distances is different for each kind of paper, the kind of paper can be identified based on a distance difference.

Example 5

In the present example, a sheet material identifying device shown in FIG. 6 was fabricated in which two vibrators 1, 1 were disposed on one side of a glossy paper and one vibration sensor 2 was disposed on the other side of the glossy paper. The vibrators 1 and the vibration sensor 2 were configured as Example 1. Further, a distance a+b between the vibrators 1 was set at 1.1 mm and a distance a between one of the vibrators 1 and the vibration sensor 2 was set at 0.6 mm. An alternating-current power supply 5 applied a voltage of 20 V to each of the vibrators 1, 1, and the frequency was similarly changed from 0 to 70 MHz. The relationship between a frequency and an amplitude of a signal detected by the vibration sensor 2 is plotted in FIG. 9. Since a difference between adjacent maximum frequencies is different for each kind of paper, the kind of paper can be identified based on a frequency difference.

Example 6

In the present example, vibrators 1, 1 and a vibration sensor 2 were arranged as Example 5, a vibration frequency was not changed and was kept at a constant vibration frequency (20 MHz), and manipulators were operated to move the vibration sensor 2. To be specific, the vibration sensor 2 was moved so as to approach one of the vibrators 1 from the midpoint position between the vibrators 1, 1, was returned to the original position, and was moved so as to approach the other vibrator 1. The relationship between an amplitude of a signal detected by the vibration sensor 2 and a distance from the reference position is plotted in FIG. 10. Since a difference between adjacent maximum distances is different for each kind of paper, the kind of paper can be identified based on a distance difference.

The vibrator 1 may be moved instead of the vibration sensor 2. For example, a distance a between one of the vibrators 1 and the vibration sensor 2 may be fixed at 0.6 mm and the other vibrator 1 may be moved. In this case, the relationship between an amplitude of a signal detected by the vibration sensor 2 and a distance b is plotted in FIG. 11. Since a difference between adjacent maximum distances is different for each kind of paper, the kind of paper can be identified based on a distance difference.

Example 7

In the present example, a sheet material identifying device shown in FIG. 7 was fabricated in which one vibrator 1 and a vibration sensor 2 were disposed on one side of a glossy paper and one vibrator 1 was disposed on the other side of the glossy paper. The vibrators 1 and the vibration sensor 2 were configured as Example 1. Further, a distance a+b between the vibrators 1 was set at 1.1 mm and a distance a between one of the vibrators 1 and the vibration sensor 2 was set at 0.6 mm. An alternating-current power supply 5 applied a voltage of 20 V to each of the vibrators 1, 1, and the frequency was similarly changed from 0 to 70 MHz. The relationship between a frequency and an amplitude of a signal detected by the vibration sensor 2 is plotted in FIG. 9. Since a difference between adjacent maximum frequencies is different for each kind of paper, the kind of paper can be identified based on a frequency difference.

Example 8

In the present example, vibrators 1, 1 and a vibration sensor 2 were arranged as Example 7, a vibration frequency was not changed and was kept at a constant vibration frequency (20 MHz), and manipulators were operated to move the vibration sensor 2. To be specific, the vibration sensor 2 was moved so as to approach one of the vibrators 1 from the midpoint position between the vibrators 1, 1 was returned to the original position, and was moved so as to approach the other vibrator 1. The relationship between an amplitude of a signal detected by the vibration sensor 2 and a distance from the reference position is plotted in FIG. 10. Since a difference between adjacent maximum distances is different for each kind of paper, the kind of paper can be identified based on a distance difference.

The vibrator 1 may be moved instead of the vibration sensor 2. For example, a distance a between one of the vibrators 1 and the vibration sensor 2 may be fixed at 0.6 mm and the other vibrator 1 may be moved. In this case, the relationship between an amplitude of a signal detected by the vibration sensor 2 and a distance b is plotted in FIG. 11. Since a difference between adjacent maximum distances is different for each kind of paper, the kind of papers can be identified based on a distance difference.

Example 9

In the present example, as shown in FIG. 13, two surface acoustic wave generating elements (vibration generating elements) 1 and one surface acoustic wave sensor (vibration sensor) 2 were brought into contact with a surface of a sheet (sheet material) P. A surface acoustic wave detecting element 2 was disposed between the two surface acoustic wave generating elements 1 so that contact points with the sheet were arranged on a straight line. The surface acoustic wave generating elements 1 and the surface acoustic wave sensor 2 were configured as shown in FIG. 16. Further, a high frequency generator (power supply) 9 was connected to the surface acoustic wave generating element 1, and an identifying section (identifying means) 3 was connected to the surface acoustic wave sensor 2.

Figure 18A:
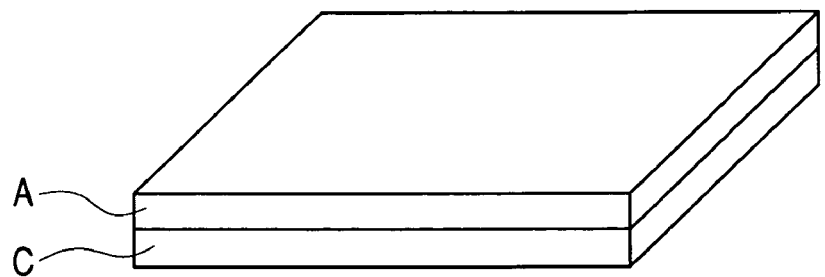
FIGS. 18A, 18B and 18C are schematic diagrams for explaining a method of fabricating the vibration generating element and the vibration sensor.
Figure 18B:
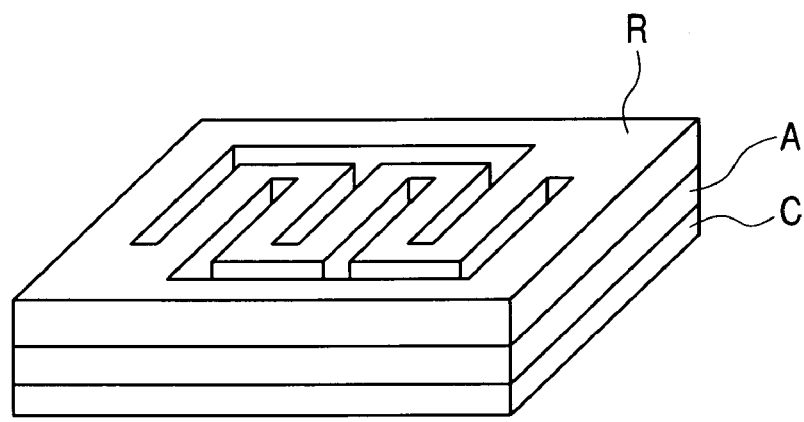
Figure 18C:
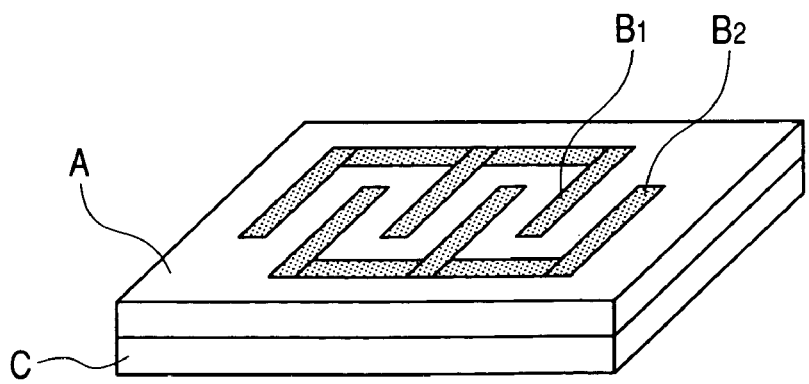

Referring to FIGS. 18A, 18B and 18C, the following will discuss a method of fabricating the surface acoustic wave generating element 1 and the surface acoustic wave sensor 2 that are used in the present example.

First, zinc oxide forming a piezoelectric body A is deposited by about 10 μm on a silicon substrate C by using the sputtering method (FIG. 18A).

Subsequently, a resist R is formed on a surface of a zinc oxide film A by using a lithography method. As shown in FIG. 18B, a pair of comb-shaped grooves is formed on the resist R and the zinc oxide film A is exposed only on parts corresponding to the grooves. Then, by using acetic acid diluted to about 33% is used to etch the zinc oxide film A by a thickness of 300 nm. Thereafter, a Pt electrode is formed with a thickness of about 300 nm by the sputtering method and the resist R is removed by using an organic solvent such as acetone and so on. Thus, as shown in FIG. 18C, electrodes B1 and B2 shaped like a pair of combs are formed on the zinc oxide film A. Additionally, the surface acoustic wave generating element 1 and the surface acoustic wave sensor 2 are about 8 mm×10 mm×0.8 mm in size.

A method of identifying papers will be discussed below.

When an alternating-current signal (alternating voltage) is applied from the high frequency generator 9 to the surface acoustic wave generating element 1, the surface acoustic wave generating element 1 generates a surface acoustic wave (surface acoustic wave with a frequency corresponding to the alternating-current signal). The surface acoustic wave is detected by the surface acoustic wave sensor 2 after propagating through the surface of a sheet.

Figure 19:
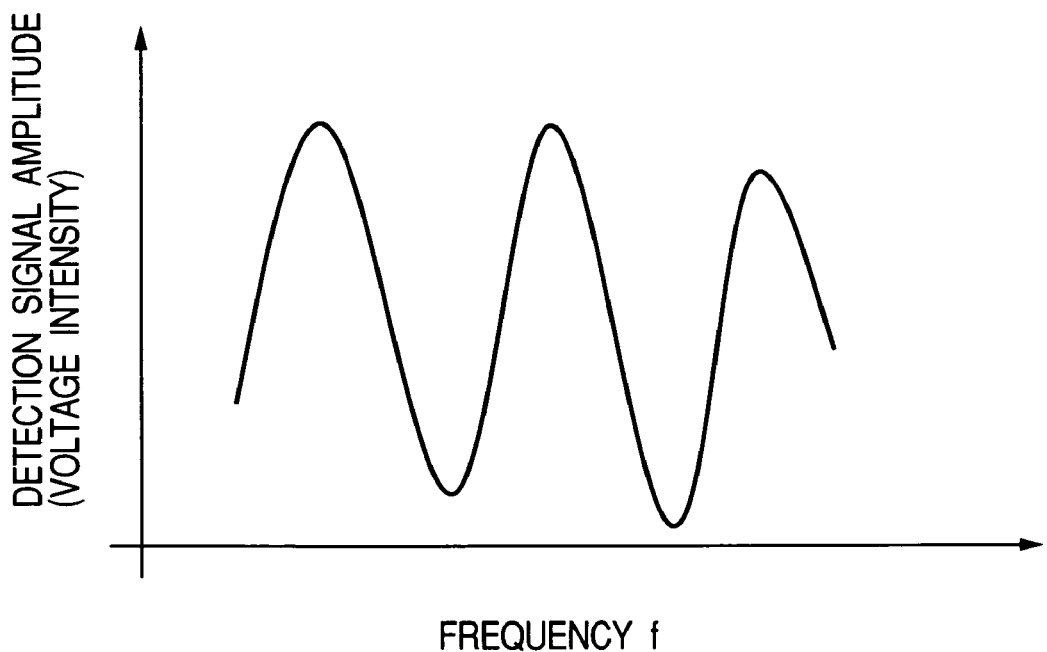
FIG. 19 is a diagram showing the relationship between an amplitude of a detection signal and a vibration frequency.

Surface acoustic waves from the surface acoustic wave generating elements 1 interfere with each other. When the frequency of the alternating-current signal is changed from 2 MHz to 5 MHz by means of the high frequency generator 9, the amplitude of a signal detected by the surface acoustic wave sensor 2 is changed as shown in FIG. 19:

at a frequency satisfying a receiving intensity maximizing condition, vibrations generated on the two surface acoustic wave generating elements 1 increase each other and the amplitude of the detection signal has a maximum value, and conversely, at a frequency satisfying a receiving intensity minimizing condition, vibrations generated on the two surface acoustic wave generating elements 1 reduce each other and the amplitude of the detection signal has a minimum value.

Each kind of paper has a different sonic speed for propagation through a sheet. Peak intervals in the graph are specific to papers. Therefore, by measuring the peak intervals of the graph, it is possible to identify the kind of paper including plain papers, overhead transparencies, coated papers and glossy papers.

Example 10

In the present example, as shown in FIG. 15, two surface acoustic wave generating elements 1 and one surface acoustic wave sensor 2 were brought into contact with a surface of a sheet (sheet material). A surface acoustic wave sensor 2 was disposed between the two surface acoustic wave generating elements 1 so that contact points with the sheet were arranged on a straight line. Further, a distance a between one of the surface acoustic wave generating elements 1 and the surface acoustic wave sensor 2 was set at 10 mm and a distance b between the other surface acoustic wave generating element 1 and the surface acoustic wave sensor 2 was also set at 10 mm. The surface acoustic wave sensor 2 was caused to move (on a straight line connecting the surface acoustic wave generating elements 1) by a driving mechanism. The surface acoustic wave generating elements 1 and the surface acoustic wave sensor 2 are similar to those of Example 9.

A method of identifying papers will be discussed below.

Figure 20:
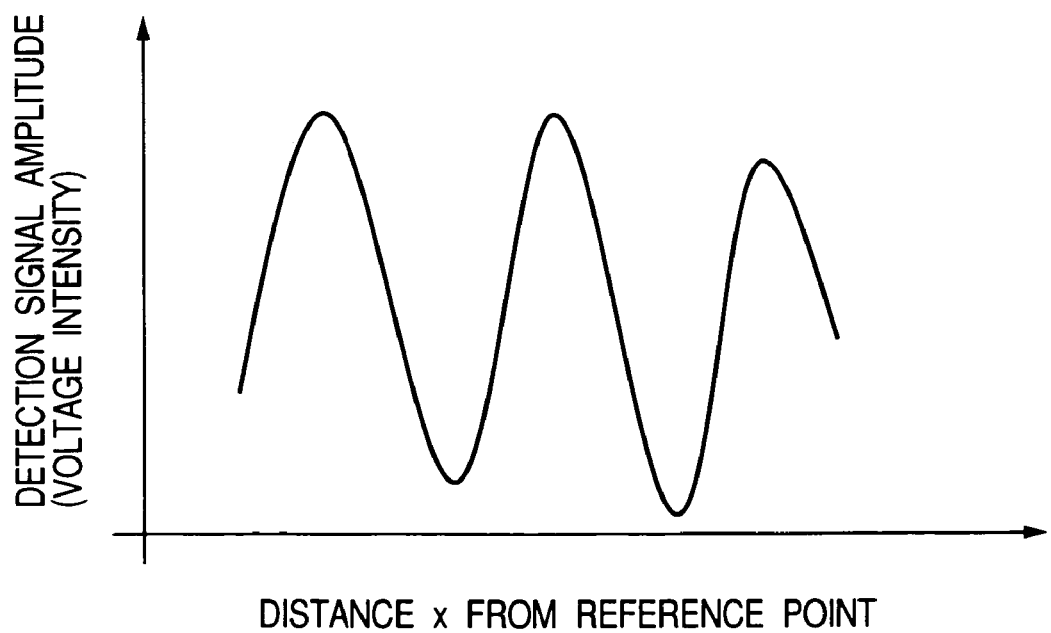
FIG. 20 is a diagram showing the relationship between an amplitude of a detection signal and a moving distance of the vibration sensor.

When surface acoustic waves with a frequency of 2 MHz are generated from the surface acoustic wave generating elements 1, the surface acoustic waves are detected by the surface acoustic wave detecting element 2 after propagating through the surface of a sheet and interfering with each other. In this state, when the surface acoustic wave sensor 2 is moved on a part which is 1 to 5 mm away from the original position, a signal detected by the surface acoustic wave sensor 2 is changed in amplitude as shown in FIG. 20.

Each kind of paper has a different sonic speed for propagation through a sheet. Peak intervals in the graph are specific to papers. Therefore, by measuring the peak intervals of the graph, it is possible to identify the kind of paper including plain papers, overhead transparencies, coated papers and glossy papers.

Example 11

In the present example, as shown in FIG. 14, two surface acoustic wave generating elements 1 and one surface acoustic wave sensor 2 were brought into contact with a surface of a sheet (sheet material). A surface acoustic wave sensor 2 was disposed between the two surface acoustic wave generating elements 1 so that contact points with the sheet were arranged on a straight line. Further, a distance a between one of the surface acoustic wave generating elements 1 and the surface acoustic wave sensor 2 was set at 10 mm and a distance b between the other surface acoustic wave generating element 1 and the surface acoustic wave sensor 2 was also set at 10 mm. One of the surface acoustic wave generating elements 1 was caused to move (on a straight line connecting the surface acoustic wave generating elements 1) by a driving mechanism. The surface acoustic wave generating elements 1 and the surface acoustic wave sensor 2 are similar to those of Example 9.

A method of identifying papers will be discussed below.

Figure 21:
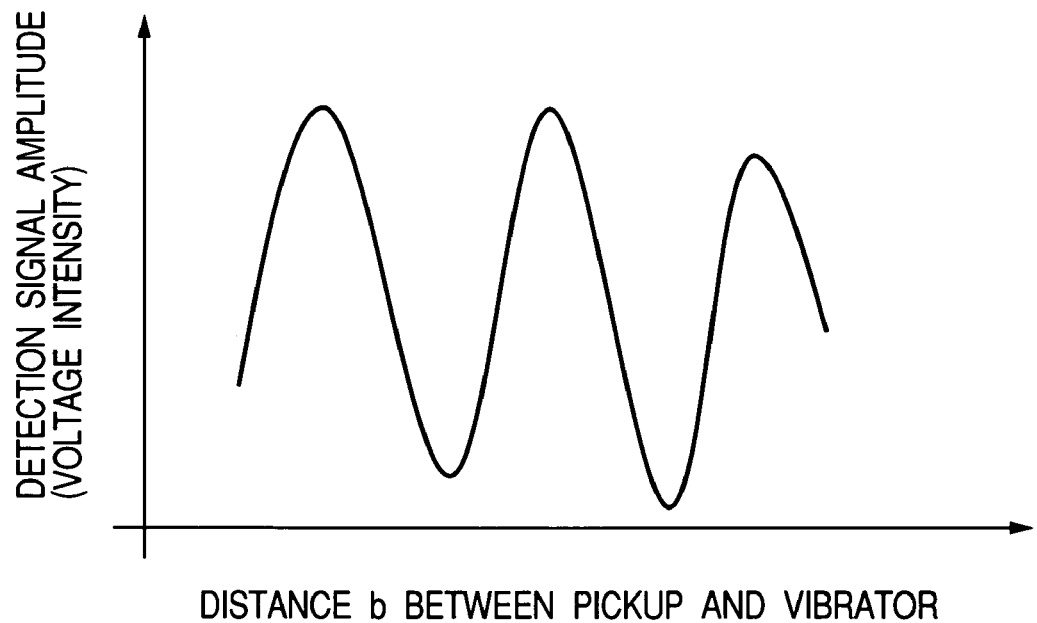
FIG. 21 is a diagram showing the relationship between an amplitude of a detection signal and a distance b (distance between the vibration sensor and the vibration generating element)

When surface acoustic waves with a frequency of 2 MHz are generated from the surface acoustic wave generating elements 1, the surface acoustic waves are detected by the surface acoustic wave detecting element 2 after propagating through the surface of a sheet and interfering with each other. In this state, when the surface acoustic wave generating element 1 is moved by 0 to 5 mm, a signal detected by the surface acoustic wave sensor 2 is changed in amplitude as shown in FIG. 21.

Each kind of paper has a different sonic speed for propagation through a sheet. Peak intervals in the graph are specific to papers. Therefore, by measuring the peak intervals of the graph, it is possible to identify the kind of paper including plain papers, overhead transparencies, coated papers and glossy papers.

Example 12

In the present example, a vibration generating element 10 for inducing vibration traveling a wide-range direction and a vibration sensor 20 for detecting vibration from a wide-range direction were used. The elements 10 and 20 were configured as shown in FIG. 17, in which a piezoelectric body D made of PZT ceramics was used and electrodes E1 and E2 made of platinum paste are formed on the two opposing surfaces of the piezoelectric body D. The piezoelectric body D is formed into a rectangular parallelepiped with a thickness (dimension between the electrodes) of 0.2 mm, and dimensions are 0.1×0.1 mm on a surface along the electrodes. Further, a convex portion F which is shaped like a hemisphere (with a radius of 0.1 mm) and is made of alumina was disposed so as to cover the electrode E2. The convex portion F was brought into contact with a sheet.

Figure 22:
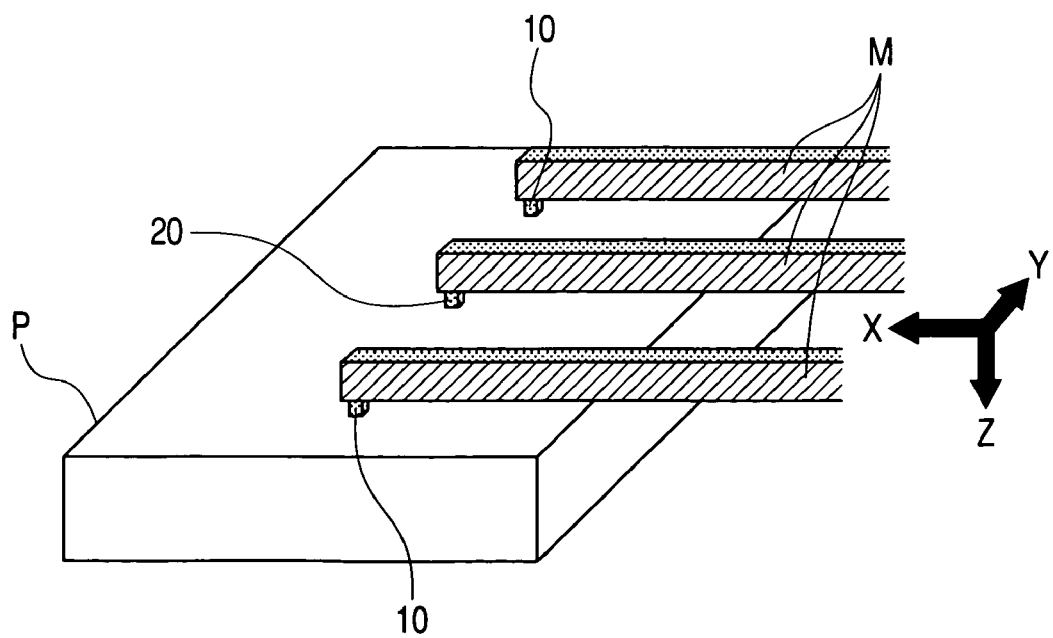
FIG. 22 is an outside perspective view showing an example of the configuration of the sheet material identifying device according to the present invention.

In the present example, as shown in FIG. 22, two vibration generating elements 10 and one vibration detecting element 20 were brought into contact with a sheet (sheet material) while being supported so as to be positioned by manipulators M. The vibration sensor 20 was disposed between the two vibration generating elements 10 so that contact points with the sheet were arranged on a straight line. An interval was set at 0.6 mm between one of the vibration generating element 10 and the vibration sensor 20, and an interval was set at 0.5 mm between the other vibration generating element 10 and the vibration sensor 20. The electrode E1 of the vibration generating element 10 was connected to a high frequency generator and the electrode E1 of the vibration sensor 20 was connected to an alternating current voltmeter.

A method of identifying papers will be discussed below.

When an alternating-current signal (alternating voltage) with an amplitude of 20 V is applied from the high frequency generator to the vibration generating element 10, the vibration generating element 10 generates an acoustic wave (acoustic wave with a frequency corresponding to the alternating-current signal). The acoustic wave is detected by the vibration sensor 20 after propagating through the surface of a sheet.

Acoustic waves from the vibration generating elements 10 interfere with each other. When the frequency of the alternating-current signal is changed from 20 MHz to 5 MHz by the high frequency generator, the amplitude of a signal detected by the vibration sensor 20 is changed as shown in FIG. 9:

in a state satisfying a receiving intensity maximizing condition, vibrations generated on the two vibration generating elements 10 increase each other and the amplitude of the detection signal has a maximum value, and conversely, in a state satisfying a receiving intensity minimizing condition, vibrations generated on the two vibration generating elements 10 reduce each other and the amplitude of the detection signal has a minimum value.

Each kind of paper has a different sonic speed for propagation through a sheet. Peak intervals in the graph are specific to papers. Therefore, by measuring the peak intervals of the graph, it is possible to identify the kind of paper including plain papers, overhead transparencies, coated papers and glossy papers.

Example 13

In the present example, vibration generating elements 10, a vibration sensor 20, and manipulators M were used that are configures as those of Example 12. Like Example 12, two vibration generating elements 10 and one vibration sensor 20 were brought into contact with a surface of a sheet (sheet material). Intervals between the vibration generating elements 10 and the vibration sensor 20 are each set at 0.55 mm. The other configurations and fabricating method are similar to those of Example 12.

When an alternating-current signal (alternating voltage with an amplitude of 20 V and a frequency of 20 MHz) is applied from a high frequency generator 4 to the vibration generating element 10, the vibration generating element 10 generates an acoustic wave (acoustic wave with a frequency corresponding to the alternating-current signal). The acoustic wave is detected by the vibration sensor 20 after propagating through the surface of a sheet.

Figure 23:
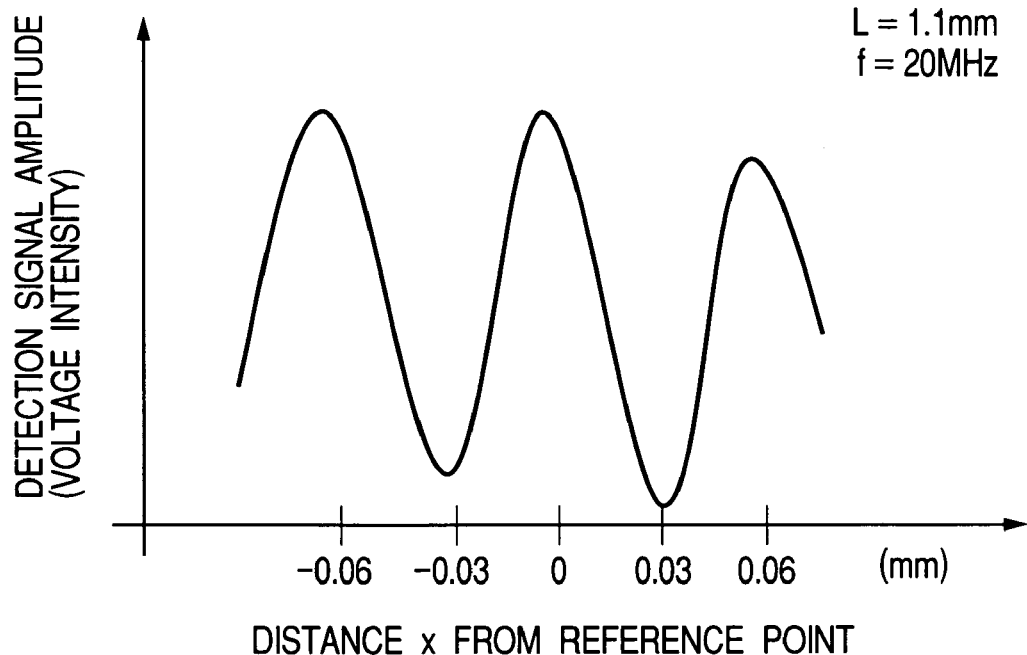
FIG. 23 is a diagram showing the relationship between an amplitude of a detection signal and a moving distance of the vibration sensor.

Acoustic waves from the vibration generating elements 10 interfere with each other. The vibration sensor 20 is moved in a range expressed by the equation below $-0.1 \text{ mm} \leq x \leq +0.1 \text{ mm}$ where x represents a moving distance from the original position, "−" represents a direction of approaching one of the vibration generating elements 10, and "+" represents a direction of approaching the other vibration generating elements 10. In this case, the amplitude of a signal detected by the vibration sensor 20 is changed as shown in FIG. 23:

in a state satisfying a receiving intensity maximizing condition, vibrations generated on the two vibration generating elements 10 increase each other and the amplitude of the detection signal has a maximum value, and conversely, in a state satisfying a receiving intensity minimizing condition, vibrations generated on the two vibration generating elements 10 reduce each other and the amplitude of the detection signal has a minimum value.

Each kind of paper has a different sonic speed for propagation through a sheet. Peak intervals in the graph are specific to papers. Therefore, by measuring the peak intervals of the graph, it is possible to identify the kind of paper including plain papers, overhead transparencies, coated papers and glossy papers.

Example 14

In the present example, vibration generating elements 10, a vibration sensor 20, and manipulators M were used that are configures as those of Example 4. Like Example 4, two vibration generating elements 10 and one vibration sensor 20 were brought into contact with a surface of a sheet (sheet material). Intervals between the vibration generating elements 10 and the vibration sensor 20 are each set at 0.55 mm. The other configurations and fabricating method are similar to those of Example 4.

When an alternating-current signal (alternating voltage with an amplitude of 20 V and a frequency of 20 MHz) is applied from a high frequency generator to the vibration generating element 10, the vibration generating element 10 generates an acoustic wave (acoustic wave with a frequency corresponding to the alternating-current signal). The acoustic wave is detected by the vibration sensor 20 after propagating through the surface of a sheet.

Figure 24:
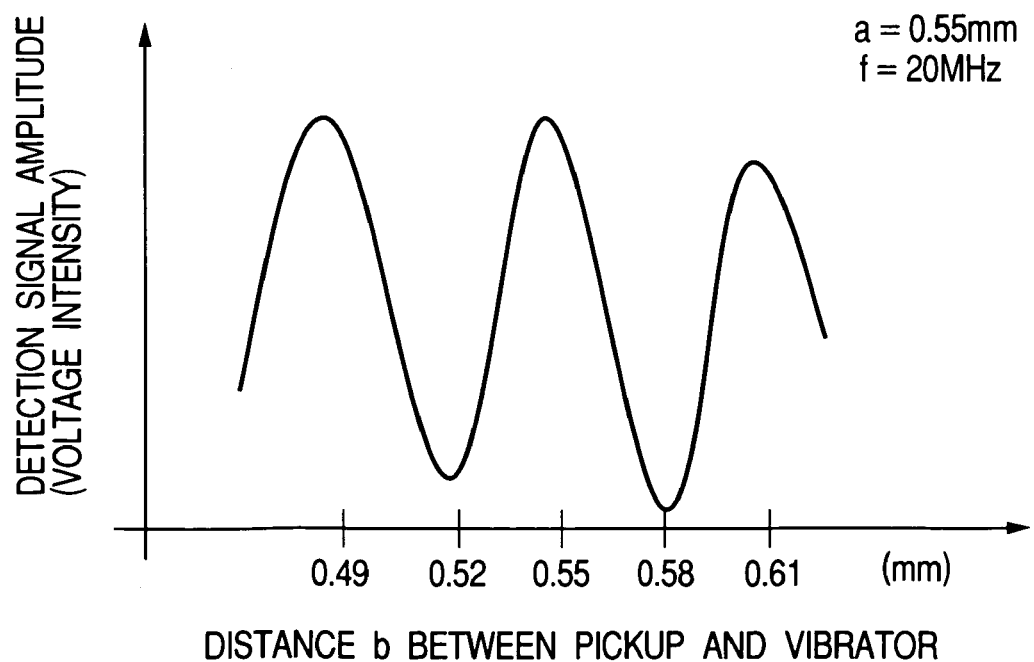
FIG. 24 is a diagram showing the relationship between an amplitude of a detection signal and a distance b (distance between the vibration sensor and the vibration generating element)

Acoustic waves from the vibration generating elements 10 interfere with each other. One of the vibration generating elements 10 is moved in a range expressed by the equation below, $$0.45\ \mathrm{mm} \leq \mathrm{distance\ b} \leq 0.65\ \mathrm{mm}$$

where a distance b represents a distance between the moving vibration generating element and the vibration sensor. In this case, the amplitude of a signal detected by the vibration sensor 20 is changed as shown in FIG. 24:

in a state satisfying a receiving intensity maximizing condition, vibrations generated on the two vibration generating elements 10 increase each other and the amplitude of the detection signal has a maximum value, and conversely, in a state satisfying a receiving intensity minimizing condition, vibrations generated on the two vibration generating elements 10 reduce each other and the amplitude of the detection signal has a minimum value.

Each kind of paper has a different sonic speed for propagation through a sheet. Peak intervals in the graph are specific to papers. Therefore, by measuring the peak intervals of the graph, it is possible to identify the kind of paper including plain papers, overhead transparencies, coated papers and glossy papers.

Example 15

Figure 25:
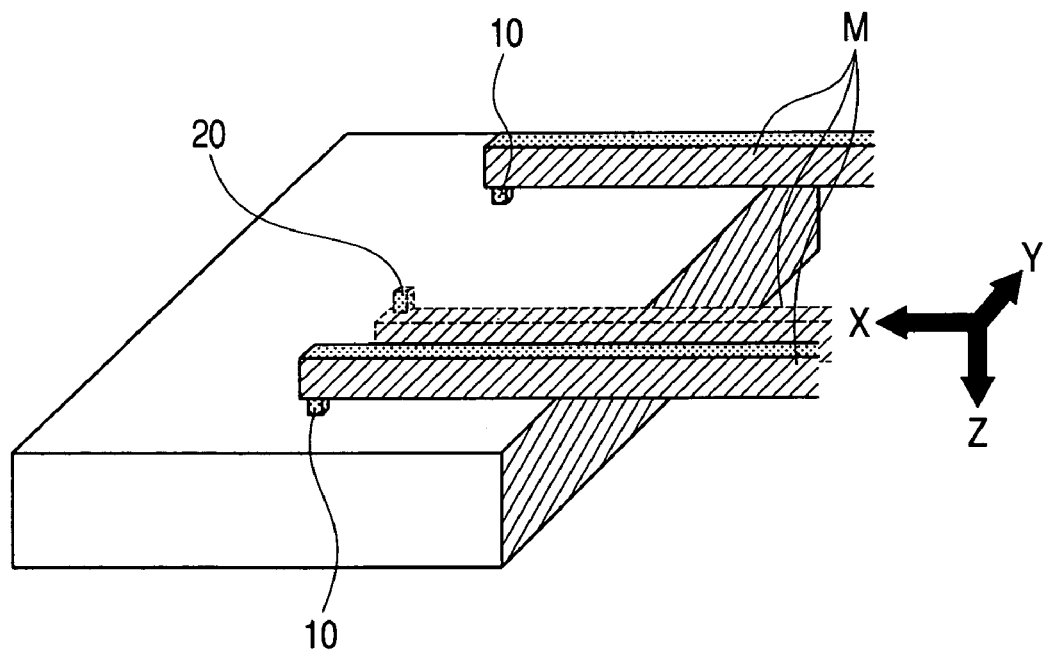
FIG. 25 is an outside perspective view showing an example of the configuration of the sheet material identifying device according to the present invention.

In the present example, vibration generating elements 10, a vibration sensor 20, and manipulators M were used that are configures as those of Example 4. As shown in FIG. 25, two vibration generating elements 10 were brought into contact with a surface of a sheet (sheet material) and one vibration sensor 20 was brought into contact with the other surface of a sheet (sheet material). The contact points of the elements were arranged on a straight line. An interval between one of the vibration generating elements 10 and the vibration sensor 20 was set at 0.6 mm and an interval between the other vibration generating element 10 and the vibration sensor 20 was set at 0.5 mm. The other configurations and fabricating method are similar to those of Example 4.

A method of identifying papers will be discussed below.

When an alternating-current signal (alternating voltage) with an amplitude of 20 V is applied from the high frequency generator to the vibration generating element 10, the vibration generating element 10 generates an acoustic wave (acoustic wave with a frequency corresponding to the alternating-current signal). The acoustic wave is detected by the vibration sensor 20 after propagating through the surface of a sheet.

Acoustic waves from the vibration generating elements 10 interfere with each other. When the frequency of the alternating-current signal is changed from 20 MHz to 50 MHz by a high frequency generator, the amplitude of a signal detected by the vibration sensor 20 is changed as shown in FIG. 9:

in a state satisfying a receiving intensity maximizing condition, vibrations generated on the two vibration generating elements 10 increase each other and the amplitude of the detection signal has a maximum value, and conversely, in a state satisfying a receiving intensity minimizing condition, vibrations generated on the two vibration generating elements 10 reduce each other and the amplitude of the detection signal has a minimum value.

Each kind of paper has a different sonic speed for propagation through a sheet. Peak intervals in the graph are specific to papers. Therefore, by measuring the peak intervals of the graph, it is possible to identify the kind of paper including plain papers, overhead transparencies, coated papers and glossy papers.

Example 16

In the present example, vibration generating elements 10, a vibration sensor 20, and manipulators M were used that are configures as those of Example 4. Like Example 15, two vibration generating elements 10 were brought into contact with a surface of a sheet (sheet material) and one vibration sensor 20 is brought into contact with the other surface of a sheet (sheet material). Intervals between the vibration generating elements 10 and the vibration sensor 20 are each set at 0.55 mm. The other configurations and fabricating method are similar to those of Example 15.

When an alternating-current signal (alternating voltage with an amplitude of 20 V and a frequency of 20 MHz) is applied from a high frequency generator to the vibration generating element 10, the vibration generating element 10 generates an acoustic wave (acoustic wave with a frequency corresponding to the alternating-current signal). The acoustic wave is detected by the vibration sensor 20 after propagating through the surface of a sheet.

Acoustic waves from the vibration generating elements 10 interfere with each other. The vibration sensor 20 is moved in a range expressed by the equation below, $$-0.1\ \mathrm{mm} \leq x \leq +0.1\ \mathrm{mm}$$

where x represents a moving distance from the original position, "−" represents a direction of approaching one of the vibration generating elements 10, and "+" represents a direction of approaching the other vibration generating elements 10. In this case, the amplitude of a signal detected by the vibration sensor 20 is changed as shown in FIG. 23:

in a state satisfying a receiving intensity maximizing condition, vibrations generated on the two vibration generating elements 10 increase each other and the amplitude of the detection signal has a maximum value, and conversely, in a state satisfying a receiving intensity minimizing condition, vibrations generated on the two vibration generating elements 10 reduce each other and the amplitude of the detection signal has a minimum value.

Each kind of paper has a different sonic speed for propagation through a sheet. Peak intervals in the graph are specific to papers. Therefore, by measuring the peak intervals of the graph, it is possible to identify the kind of paper including plain papers, overhead transparencies, coated papers and glossy papers.

Example 17

In the present example, vibration generating elements 10, a vibration sensor 20, and manipulators M were used that are configures as those of Example 4. Like Example 15, two vibration generating elements 10 were brought into contact with a surface of a sheet (sheet material) and one vibration sensor 20 is brought into contact with the other surface of a sheet (sheet material). Intervals between the vibration generating elements 10 and the vibration sensor 20 are each set at 0.55 mm. The other configurations and fabricating method are similar to those of Example 4.

When an alternating-current signal (alternating voltage with an amplitude of 20 V and a frequency of 20 MHz) is applied from a high frequency generator to the vibration generating element 10, the vibration generating element 10 generates an acoustic wave (acoustic wave with a frequency corresponding to the alternating-current signal). The acoustic wave is detected by the vibration sensor 20 after propagating through the surface of a sheet.

Acoustic waves from the vibration generating elements 10 interfere with each other. One of the vibration generating elements 10 is moved in a range expressed by the equation below, $$0.45 \text{ mm} \leq \text{distance b} \leq 0.65 \text{ mm}$$

where a distance b represents a distance between the moving vibration generating element and the vibration sensor. In this case, the amplitude of a signal detected by the vibration sensor 20 is changed as shown in FIG. 24:

in a state satisfying a receiving intensity maximizing condition, vibrations generated on the two vibration generating elements 10 increase each other and the amplitude of the detection signal has a maximum value, and conversely, in a state satisfying a receiving intensity minimizing condition, vibrations generated on the two vibration generating elements 10 reduce each other and the amplitude of the detection signal has a minimum value.

Each kind of paper has a different sonic speed for propagation through a sheet. Peak intervals in the graph are specific to papers. Therefore, by measuring the peak intervals of the graph, it is possible to identify the kind of paper including plain papers, overhead transparencies, coated papers and glossy papers.

Example 18

Figure 26:
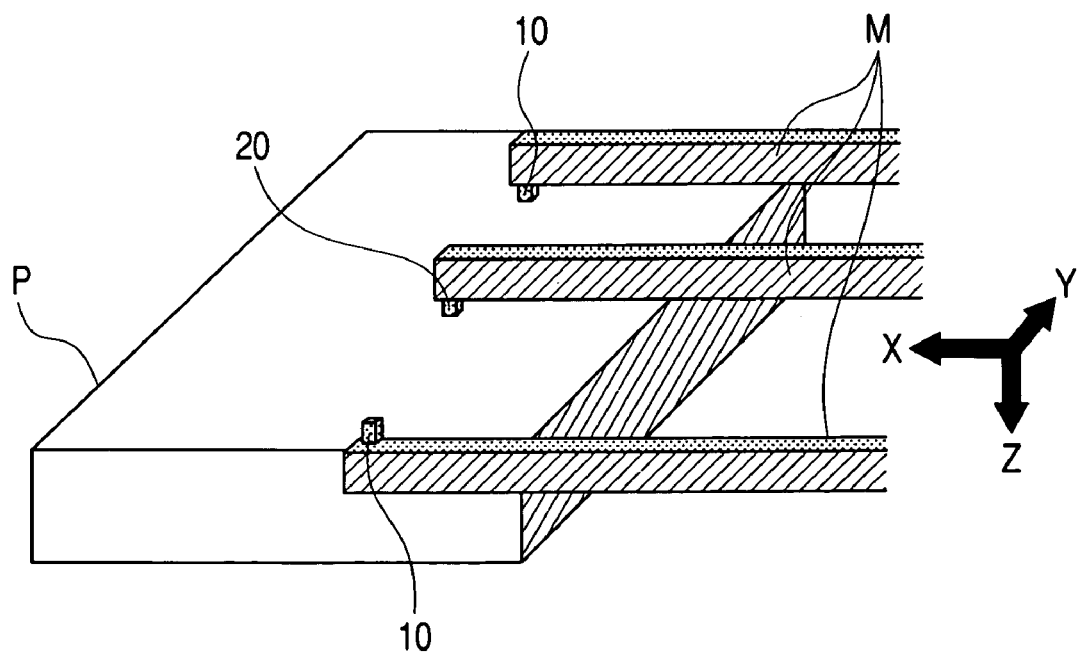
FIG. 26 is an outside perspective view showing an example of the configuration of the sheet material identifying device, according to the present invention.

In the present example, vibration generating elements 10, a vibration sensor 20, and manipulators M were used that are configures as those of Example 4. As shown in FIGS. 26 and 8, one vibration generating element 10 and one vibration sensor 20 were brought into contact with a surface of a sheet(sheet material) and one vibration generating element 10 was brought into contact with the other surface of the sheet. The contact points of the elements were arranged on a straight line. An interval between one of the vibration generating elements 10 and the vibration sensor 20 was set at 0.6 mm and an interval between the other vibration generating element 10 and the vibration sensor 20 was set at 0.5 mm. The other configurations and fabricating method are similar to those of Example 4.

A method of identifying papers will be discussed below.

When an alternating-current signal (alternating voltage) with an amplitude of 20 V is applied from a high frequency generator to the vibration generating element 10, the vibration generating element 10 generates an acoustic wave (acoustic wave with a frequency corresponding to the alternating-current signal). The acoustic wave is detected by the vibration sensor 20 after propagating through the surface of a sheet.

Acoustic waves from the vibration generating elements 10 interfere with each other. When the frequency of the alternating-current signal is changed from 20 MHz to 50 MHz by a high frequency generator, the amplitude of a signal detected by the vibration sensor 20 is changed as shown in FIG. 9:

in a state satisfying a receiving intensity maximizing condition, vibrations generated on the two vibration generating elements 10 increase each other and the amplitude of the detection signal has a maximum value, and conversely, in a state satisfying a receiving intensity minimizing condition, vibrations generated on the two vibration generating elements 10 reduce each other and the amplitude of the detection signal has a minimum value.

Each kind of paper has a different sonic speed for propagation through a sheet. Peak intervals in the graph are specific to papers. Therefore, by measuring the peak intervals of the graph, it is possible to identify the kind of paper including plain papers, overhead transparencies, coated papers and glossy papers.

Example 19

In the present example, vibration generating elements 10, a vibration sensor 20, and manipulators M were used that are configures as those of Example 4. Like Example 18, one vibration generating element 10 and one vibration sensor 20 were brought into contact with a surface of a sheet (sheet material) and one vibration generating element 10 was brought into contact with the other surface of the sheet. Intervals between the vibration generating elements 10 and the vibration detecting element 20 were each set at 0.55 mm. The other configurations and fabricating method are similar to those of Example 10.

When an alternating-current signal (alternating voltage with an amplitude of 20 V and a frequency of 20 MHz) is applied from a high frequency generator to the vibration generating element 10, the vibration generating element 10 generates an acoustic wave (acoustic wave with a frequency corresponding to the alternating-current signal). The acoustic wave is detected by the vibration sensor 20 after propagating through the surface of a sheet.

Acoustic waves from the vibration generating elements 10 interfere with each other. The vibration sensor 20 is moved in a range expressed by the equation below, $$-0.1 \text{ mm} \leq x \leq +0.1 \text{ mm}$$

where x represents a moving distance from the original position, "−" represents a direction of approaching one of the vibration generating elements 10, and "+" represents a direction of approaching the other vibration generating elements 10. In this case, the amplitude of a signal detected by the vibration sensor 20 is changed as shown in FIG. 24:

in a state satisfying a receiving intensity maximizing condition, vibrations generated on the two vibration generating elements 10 increase each other and the amplitude of the detection signal has a maximum value, and conversely, in a state satisfying a receiving intensity minimizing condition, vibrations generated on the two vibration generating elements 10 reduce each other and the amplitude of the detection signal has a minimum value.

Each kind of paper has a different sonic speed for propagation through a sheet. Peak intervals in the graph are specific to papers. Therefore, by measuring the peak intervals of the graph; it is possible to identify the kind of paper including plain papers, overhead transparencies, coated papers and glossy papers.

Example 20

In the present example, vibration generating elements 10, a vibration sensor 20, and manipulators M were used that are configures as those of Example 4. Like Example 18, one vibration generating element 10 and one vibration sensor 20 were brought into contact with a surface of a sheet (sheet material) and one vibration generating element 10 was brought into contact with the other surface of the sheet. Intervals between the vibration generating elements 10 and the vibration detecting element 20 were each set at 0.55 mm. The other configurations and fabricating method are similar to those of Example 10.

When an alternating-current signal (alternating voltage with an amplitude of 20 V and a frequency of 20 MHz) is applied from a high frequency generator to the vibration generating element 10, the vibration generating element 10 generates an acoustic wave (acoustic wave with a frequency corresponding to the alternating-current signal). The acoustic wave is detected by the vibration sensor 20 after propagating through the surface of a sheet.

Acoustic waves from the vibration generating elements 10 interfere with each other. One of the vibration generating elements 10 is moved in a range expressed by the equation below, 0.45 mm≦distance b≦0.65 mm where a distance b represents a distance between the moving vibration generating element and the vibration sensor. In this case, the amplitude of a signal detected by the vibration sensor 20 is changed as shown in FIG. 24:

in a state satisfying a receiving intensity maximizing condition, vibrations generated on the two vibration generating elements 10 increase each other and the amplitude of the detection signal has a maximum value, and conversely, in a state satisfying a receiving intensity minimizing condition, vibrations generated on the two vibration generating elements 10 reduce each other and the amplitude of the detection signal has a minimum value.

Each kind of paper has a different sonic speed for propagation through a sheet. Peak intervals in the graph are specific to papers. Therefore, by measuring the peak intervals of the graph, it is possible to identify the kind of paper including plain papers, overhead transparencies, coated papers and glossy papers.

What is claimed is:

1. A recording medium identifying device for identifying the kind of recording medium for an image forming apparatus by applying vibration on the recording medium, comprising:
    a vibrator for applying vibration on the recording medium,
    a vibration sensor for detecting, via the recording medium, vibration applied by the vibrator;
    means for changing a vibrating state between the vibrator and the vibration sensor; and
    an identifying section for identifying the kind of recording medium based on a detection result of the vibration sensor,
    wherein the identifying section identifies the recording medium based on a difference between a frequency where a detection signal outputted from the vibration sensor has a maximum value and a frequency where the detection signal has another maximum value, a difference between a frequency where the detection signal has a minimum value and a frequency where the detection signal has another minimum value, or a difference between a frequency where the detection signal has a maximum value and a frequency where the detection signal has a minimum value.

2. The recording medium identifying device according to claim 1, wherein said means for changing the vibrating state changes a vibration frequency applied by the vibrator.

3. The recording medium identifying device according to claim 2, wherein said means for changing the vibration state changes the vibration frequency without changing the vibrator and the vibration sensor in position.

4. The recording medium identifying device according to claim 1, wherein the vibrator and the vibration sensor are disposed respectively on both sides of the recording medium.

5. The recording medium identifying device according to claim 1, wherein the vibrator and the vibration sensor are disposed on one side of the recording medium.

6. The recording medium identifying device according to claim 1, further comprising a plurality of vibrators each having a different distance from the vibration sensor,
    wherein said means for changing a vibration state simultaneously changes a frequency of said plurality of vibrators.

7. The recording medium identifying device according to claim 1, wherein the vibrator is an element for generating a surface acoustic wave and the vibration sensor is an element for detecting a surface acoustic wave.

8. An image forming apparatus, comprising:
    the recording medium identifying device according to claim 1, and
    an image forming section for forming an image on a recording medium based on information corresponding to the kind of recording medium identified by the recording medium identifying device.

* * * * *